United States Patent
Balch et al.

(10) Patent No.: US 7,475,684 B2
(45) Date of Patent: *Jan. 13, 2009

(54) THERMAL VAPORIZATION APPARATUS AND METHOD

(75) Inventors: Bertram A. Balch, Venice, CA (US); Daniel G. Seng, Venice, CA (US)

(73) Assignee: Vaporbrothers, Inc., Bloomington, IN (US)

( * ) Notice: Subject to any disclaimer, the term of this patent is extended or adjusted under 35 U.S.C. 154(b) by 453 days.

This patent is subject to a terminal disclaimer.

(21) Appl. No.: 10/871,239

(22) Filed: Jun. 18, 2004

(65) Prior Publication Data

US 2005/0117895 A1  Jun. 2, 2005

Related U.S. Application Data

(63) Continuation-in-part of application No. 10/256,633, filed on Sep. 27, 2002.

(60) Provisional application No. 60/326,027, filed on Sep. 29, 2001.

(51) Int. Cl.
| | |
|---|---|
| *A61M 15/00* | (2006.01) |
| *A61M 16/10* | (2006.01) |
| *A61M 16/00* | (2006.01) |
| *H05B 3/00* | (2006.01) |
| *A62B 7/00* | (2006.01) |
| *F24J 3/00* | (2006.01) |

(52) U.S. Cl. ............... 128/203.16; 128/203.27; 128/204.17

(58) Field of Classification Search ............ 128/203.26, 128/202.21, 204.17, 203.27, 204.13, 204.14, 128/203.16; 131/273, 190, 193–194, 196, 131/173; D27/162

See application file for complete search history.

(56) References Cited

U.S. PATENT DOCUMENTS

| 87,603 | A | 3/1869 | Tichenor |
|---|---|---|---|
| 107,495 | A | 9/1870 | Hitselberger |
| 110,594 | A | 12/1870 | Selfe |
| 1,579,703 | A | 4/1926 | Grant |
| 1,609,553 | A | 12/1926 | King |
| 1,849,795 | A | 3/1932 | Fenton |
| 1,858,580 | A | 5/1932 | Collins |
| 2,808,494 | A | 10/1957 | Telkes |
| 2,815,030 | A | 12/1957 | Wenger |
| 3,152,240 | A | 10/1964 | Scott |

(Continued)

OTHER PUBLICATIONS

Internet, Eterra, http://www.lightwell.net/photos.html, printed Sep. 22, 2003 (2 pages).

(Continued)

*Primary Examiner*—Justine R Yu
*Assistant Examiner*—Kristen C Matter
(74) *Attorney, Agent, or Firm*—Christie, Parker & Hale, LLP

(57) ABSTRACT

A vaporizer apparatus for vaporizing medical herbs and essences is described that uses an electrical power driven medium to vaporize the herbs and essences. The vaporizer apparatus has a heating element assembly disposed within a shield. The shield is disposed within an opening of an enclosure. The shield protrudes from the opening at an angle and has a mating section for mating with a hand piece. The hand piece includes a vaporization chamber where herbs are packed, an inlet for connecting with the mating section of the shield, and an outlet for inhalation by a user. Methods for using the vaporizer apparatus is also discussed.

36 Claims, 19 Drawing Sheets

U.S. PATENT DOCUMENTS

| | | | |
|---|---|---|---|
| 3,543,768 A | | 12/1970 | Law |
| 3,703,179 A | | 11/1972 | Nubla |
| 3,803,004 A | | 4/1974 | Egri |
| 3,804,100 A | | 4/1974 | Fariello |
| 3,805,806 A | | 4/1974 | Grihalva |
| 3,863,646 A | | 2/1975 | Kahler |
| 3,881,499 A | | 5/1975 | McFadden et al. |
| 3,882,875 A | | 5/1975 | Frost |
| 3,889,690 A | * | 6/1975 | Guarnieri .................. 131/185 |
| 3,902,506 A | | 9/1975 | Hawie |
| 4,014,353 A | | 3/1977 | Kahler |
| 4,029,109 A | | 6/1977 | Kahler |
| 4,036,240 A | | 7/1977 | Murray, Jr. |
| 4,044,781 A | | 8/1977 | Heggestuen |
| 4,071,035 A | | 1/1978 | Boyd et al. |
| D247,255 S | | 2/1978 | Frost |
| 4,096,868 A | | 6/1978 | Norman |
| 4,111,213 A | | 9/1978 | Shanto et al. |
| 4,111,214 A | | 9/1978 | Flesher |
| 4,133,318 A | * | 1/1979 | Gross et al. ............... 131/173 |
| 4,134,409 A | | 1/1979 | McManus |
| 4,142,536 A | | 3/1979 | DeCarlo |
| 4,148,327 A | | 4/1979 | Graham |
| 4,161,954 A | | 7/1979 | Fornaciari |
| 4,198,993 A | | 4/1980 | Martin et al. |
| 4,201,230 A | | 5/1980 | Howell, Jr. |
| 4,219,032 A | | 8/1980 | Tabatznik et al. |
| 4,648,410 A | | 3/1987 | Seroussi |
| 4,682,610 A | | 7/1987 | Freelain |
| 4,899,766 A | | 2/1990 | Ross, Jr. |
| 4,922,901 A | * | 5/1990 | Brooks et al. ........ 128/203.26 |
| 4,947,875 A | | 8/1990 | Brooks et al. |
| 5,016,654 A | | 5/1991 | Bernasek et al. |
| 5,038,802 A | | 8/1991 | White et al. |
| 5,080,113 A | | 1/1992 | Bui |
| 5,235,992 A | | 8/1993 | Sensabaugh, Jr. |
| 5,458,106 A | | 10/1995 | Kim |
| 5,564,442 A | | 10/1996 | MacDonald et al. |
| 5,649,554 A | | 7/1997 | Sprinkel et al. |
| 5,693,270 A | * | 12/1997 | Moore et al. ............... 264/21 |
| 5,738,116 A | | 4/1998 | Truelove |
| 5,993,748 A | * | 11/1999 | Wheeler ..................... 422/125 |
| 6,026,820 A | | 2/2000 | Baggett, Jr. et al. |
| 6,067,993 A | | 5/2000 | Mahoney, III |
| 6,073,632 A | | 6/2000 | Tolja |
| 6,095,153 A | | 8/2000 | Kessler et al. |
| 6,250,301 B1 | | 6/2001 | Pate |
| 6,354,301 B2 | | 3/2002 | McCoy |
| 6,431,176 B1 | | 8/2002 | Rice |
| 2003/0217750 A1 | | 11/2003 | Amirpour et al. |

OTHER PUBLICATIONS

Internet, Eterra, http://www.lightwell.net/classic.html, printed Sep. 22, 2003 (2 pages).

Internet, http://www.lightwell.net/tulip/tuliptop.jpg, printed Sep. 22, 2003 (1 page).

Internet, http://www.lightwell.net/tulip/tulip-caddy-1-.gif, printed Sep. 22, 2003 (1 page).

Internet, http://www.vaporwarehouse.com/store/shop?1=1&p=vapordoc.html, "Vapor Doc Vaporizer", Jul. 25, 2003, USA (1 page).

Tandem Dream", Small Vaporizer", Issue 40, Sep. 2003, USA (2 pages).

Vapor Visions, "Vapor Visions" Vaporizer, USA (1 page).

Internet, http://www.vapordoc.com/catalog/product_info.php?products_id=28&osCsid=dbdbfbd68, "Standard Vaporizer Kit", Apr. 20, 2004, USA (2 pages).

Internet, http://www.overgrown.com/vaporizer.php, "Herbal Vaporizers", Issue 40, Jul. 25, 2003, USA (2 pages).

Internet, http://www.vaportechco.com/meth.html, "Vaping Methods", Jan. 19, 2004, USA (4 pages).

Internet, http://www.bcvaporizer.com/history.html, "The Amazing BC Vaporizer", Mar. 24, 2004, Vancouver, British Columbia (2 pages).

Final Office Action for U.S. Appl. No. 10/256,633, filed Sep. 27, 2002, inventor Bertram A. Balch, Final Office Action mailed Aug. 11, 2006 (17 pages).

Office Action for U.S. Appl. No. 10/256,633, filed Sep. 27, 2002, inventor Bertram A. Balch, Office Action Mailed Jan. 24, 2006 (24 pages).

* cited by examiner

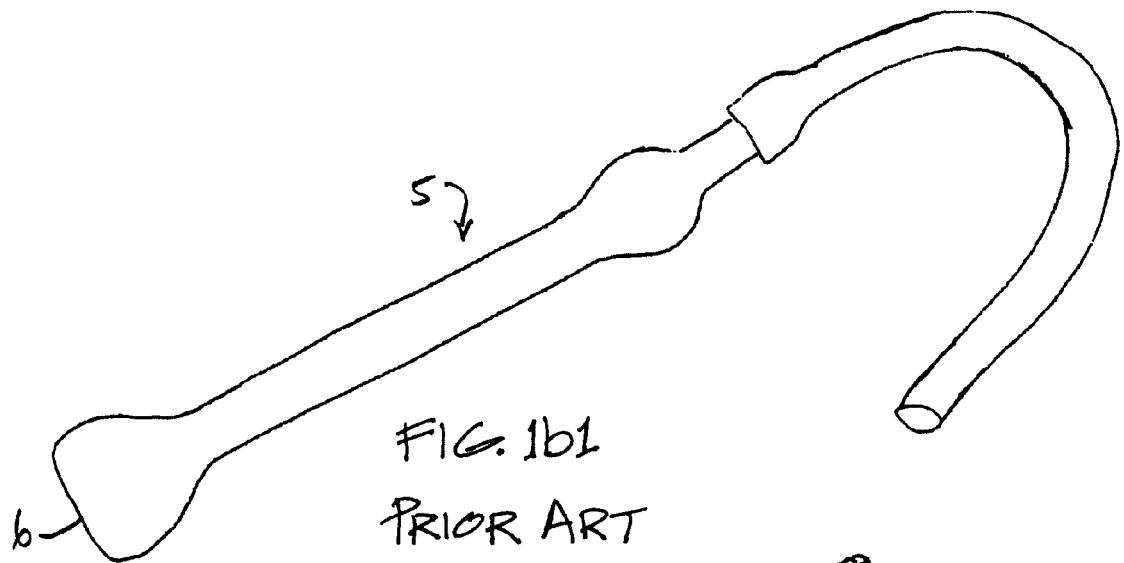
FIG. 1b1
PRIOR ART
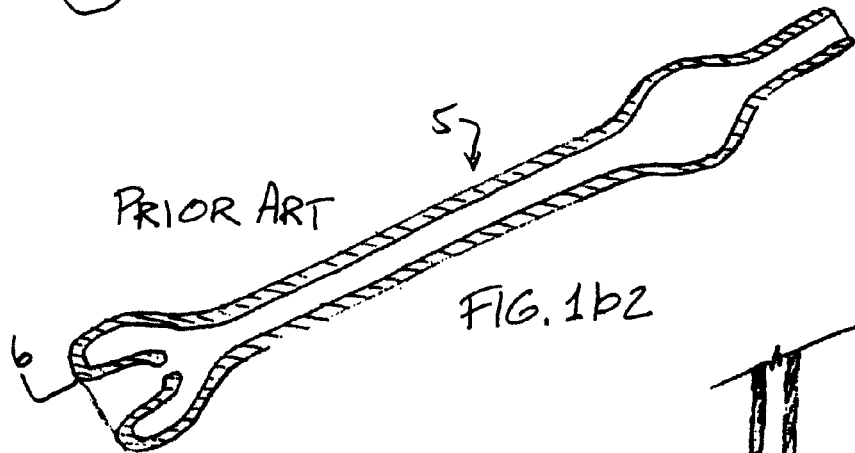
PRIOR ART
FIG. 1b2
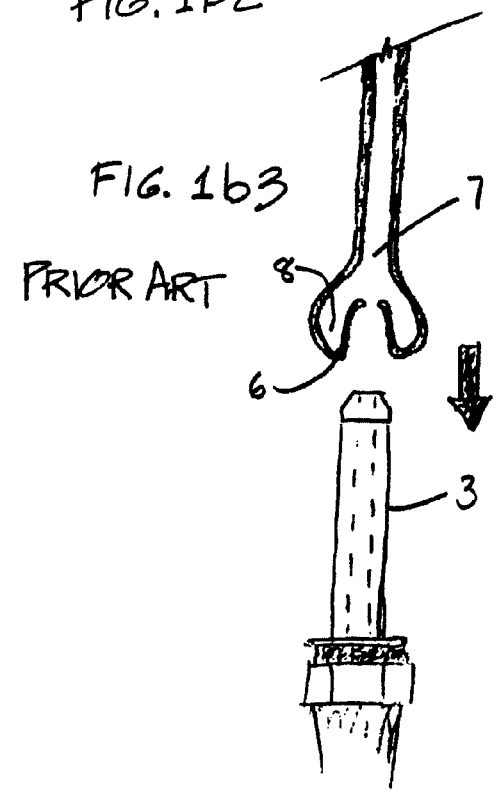
FIG. 1b3
PRIOR ART

THERMAL VAPORIZATION APPARATUS AND METHOD

CROSS REFERENCE TO RELATED APPLICATION

This is a continuation-in-part application of Ser. No. 10/256,633, filed on Sep. 27, 2002, entitled THERMAL VAPORIZATION APPARATUS AND METHOD, which claims priority to provisional application Ser. No. 60/326,027, filed on Sep. 29, 2001, entitled THERMAL ATOMIZATION AND VAPORIZATION TECHNIQUE FOR MASS TRANSPORTATION OF BOTANICAL SPECIMENS USING AN INSTANT VAPORIZER, the contents of the related applications are hereby expressly incorporated herein by reference as if set forth in full.

Thermal vaporization devices discussed herein generally relate to devices for vaporizing carriers, such as medicine herbs and flower essences, for inhalation; and more specifically to thermal vaporization devices which include an electrically driven heating chamber for heating and vaporizing fragrances and aroma from the vapor releasing carriers.

BACKGROUND

Vaporizing carriers for aroma-therapy such as medicine herbs and flower essences to release active elements and essences is well known in the art. In general, the vaporization process includes directly burning a carrier in a pipe and then inhaling the smoke released from the burnt carrier. Alternatively, for inhaling cooler and filtered smoke, a smoking device having a water reservoir is used to filter the vaporized smoke before inhalation.

Plants have been used for their medicinal properties and aroma-therapies for many years. In fact, the majority of medicines used today are either derived directly from plants or synthesized as variations of natural molecules derived therefrom. When vaporized essences and fragrances are inhaled, several benefits are derived including directly applying the active ingredients to the pulmonary tract to treat diseases such as asthma and bronchitis. Drug inhalation also circumvents the "first-pass effect", which typically occurs when drugs are taken orally and processed by the intestines and then partially or entirely metabolized by the liver before entering the blood stream.

In addition to using plants and flowers for curing diseases, flower essences and fragrances are believed to provide therapeutic qualities as they are thought to work on an emotional level to harmonize negative feelings and belief patterns held in the subconscious mind. On the Australian Bush Flower Essences website, at www.ausflowers.com/au, it was reported that the Australian Aborigines and the Ancient Egyptians have always used flowers to heal their emotions. The effect of these essences or fragrances is similar to that of meditation in that they enable the meditating party to access his or her subconscious mind to allow positive virtues such as love, joy, faith, courage, etc. to flood his or her souls.

Examples of prior smoking apparatus include U.S. Pat. No. 87,603 to Tichenor, which discloses a device for continuously heating or pyrolizing a substance on a grating, and U.S. Pat. No. 1,858,580 to Collins, which discloses a smoking apparatus that uses steam to vaporize carriers by heating a water chamber with a heating coil. Another example includes U.S. Pat. No. 6,250,301 to Pate, which discloses a vaporizer apparatus for uniformly extracting active ingredients from a specimen without pyrolysis. The '301 patent uses hot air or a heated inert gas stream to vaporize the specimen for inhalation. The heated air or gas is introduced to the device from the device's lower portion (from either a hot air gun or a high pressure tank connected to a heat exchanger) and ascends through a permeable support structure (e.g., fritted glass disk, etc.). The gas causes specimen particles disposed on the permeable support structure to be suspended within the confines of an isolation chamber for inhalation.

FIG. 1*a* is a prior art vaporizer device 1 manufactured by the inventors of the present invention. Although the prior art vaporizer device 1 was effective and was well received, it had several shortcomings. Among other things, the housing 2 does not have any ventilation other than the top opening. Thus, the prior art housing 2 must be sufficiently large relative to the heating element 3 to ensure sufficient air circulation. This places constraints on the housing size, shape, and configuration. In addition, the heating element 3 was mounted vertical within the housing 2 and with respect to the base. Accordingly, when the vaporizer device 1 is used, the herbs tend to fall out of the vaporizing chamber (not shown) into the heating element 3 where they can ignite.

Another shortcoming of the prior art vaporizer device 1 is the inability to view the heating element while the same is being used. Consequently, it is difficult to discern how much of the control knob 4 to adjust or turn to regulate the amount of heat generated by the heating element 3 during use. Finally, the prior art hand piece 5 (FIGS. 1*b*1 - 1*b*3) used in combination with the prior art vaporizer device 1 similarly suffers from several shortcomings. For example, the inlet end comprises a deep well for receiving the heating element 3. Due to the configuration, a vaporization chamber 7 is not readily accessible. This makes the prior art hand piece 5 both difficult to use (i.e., to pack) and to clean. Furthermore, the design does not allow for an efficient intake air to herb contact, as some of the herbs will dislodge within the end space 8 of the hand piece 5.

Therefore, it would be desirable to develop a vaporizer that efficiently vaporizes carriers for mass transportation of botanical fragrances in the field of aroma-therapy that is also relatively inexpensive and without the shortcomings experienced by the prior art devices.

SUMMARY

The present invention is directed to vaporizer devices that vary in functions and constructions as provided further below. In one exemplary embodiment, there is provided a vaporizer device, which may be characterized by an apparatus for extracting active ingredients from a specimen, the vaporizer apparatus comprising a housing comprising a plurality of housing walls, an interior space defined by a plurality of housing walls, and at least two openings formed upon the housing walls; a heating element assembly operable with electrical power; and a shield having a body section for covering at least a portion of the heating element assembly, said shield being held in said interior space by a holding structure attached to said housing.

In another aspect of the present invention, there is provided a vaporizer comprising a heating element assembly operable with electrical power; a shield having a substantially cylindrical body section, an exterior surface, and an interior surface defining an interior cavity for receiving the heating element assembly; a housing defining an interior space comprising at least two openings; and wherein said shield is held within said interior space of said housing by a portion of the housing encapsulating at least a portion of the exterior surface of the shield.

The present invention also discloses a method of using the vaporizer apparatus. The method includes assembling a housing comprising a plurality of housing walls and an interior space defined by the plurality of housing walls; holding a shield comprising a first opening and a second opening with a support member positioned inside the interior space of the housing; and inserting a heating element assembly operable with electrical power into the second opening of the shield.

BRIEF DESCRIPTION OF THE DRAWINGS

The invention is best understood from the following detailed description when read in conjunction with the accompanying drawings. It is emphasized that, according to common practice, the various features of the drawings are not to scale. On the contrary, the dimensions of the various features are arbitrarily expanded or reduced for clarity. Like numerals denote like features throughout the specification and drawings. Included are the following figures:

FIGS. 1b1- 1b3 set forth several views of a prior art hand piece.

FIG. 1 is a semi-schematic cross-sectional view of an exemplary embodiment of a vaporizer apparatus of the present invention;

FIG. 3 is a semi-schematic exploded perspective view of a heating element assembly as shown in FIGS. 1 and 2;

DETAILED DESCRIPTION

The detailed description set forth below in connection with the appended drawings is intended as a description of the presently preferred embodiments of the thermal vaporization devices provided in accordance with the present invention and is not intended to represent the only forms in which the present invention may be constructed or utilized. The description sets forth the features and the steps for constructing and using thermal vaporization devices of the present invention in connection with the illustrated embodiments. It is to be understood, however, that the same or equivalent functions and structures may be accomplished by different embodiments, which are also intended to be encompassed within the spirit and scope of the invention. Also, as denoted elsewhere herein, like element numbers are intended to indicate like or similar elements or features.

The present invention relates to an apparatus and a method for vaporizing herbs, natural products, floral essences, etc. that preferably have high moisture and oil contents. Collectively, these substances will be referred to as carriers or herbs, which when heated emit smoke containing medicinal and/or therapeutic qualities.

Broadly speaking, the present invention comprises an electrical heating element contained in a heating chamber, which emit radiation, convection and conduction heat to the intake air. The heated intake air then passes through a vaporizing chamber, which contains a desired amount of herbs, to vaporize the herbs. A control switch for controlling the amount of heat generated by the heating element to heat the intake air is preferably used to regulate the heating element. Vaporized aroma and essences, i.e., smoke, are then carried out of the herbs by negative air pressure generated by the user, which are then inhaled by the user for the desired therapeutic effects.

Figure 1:
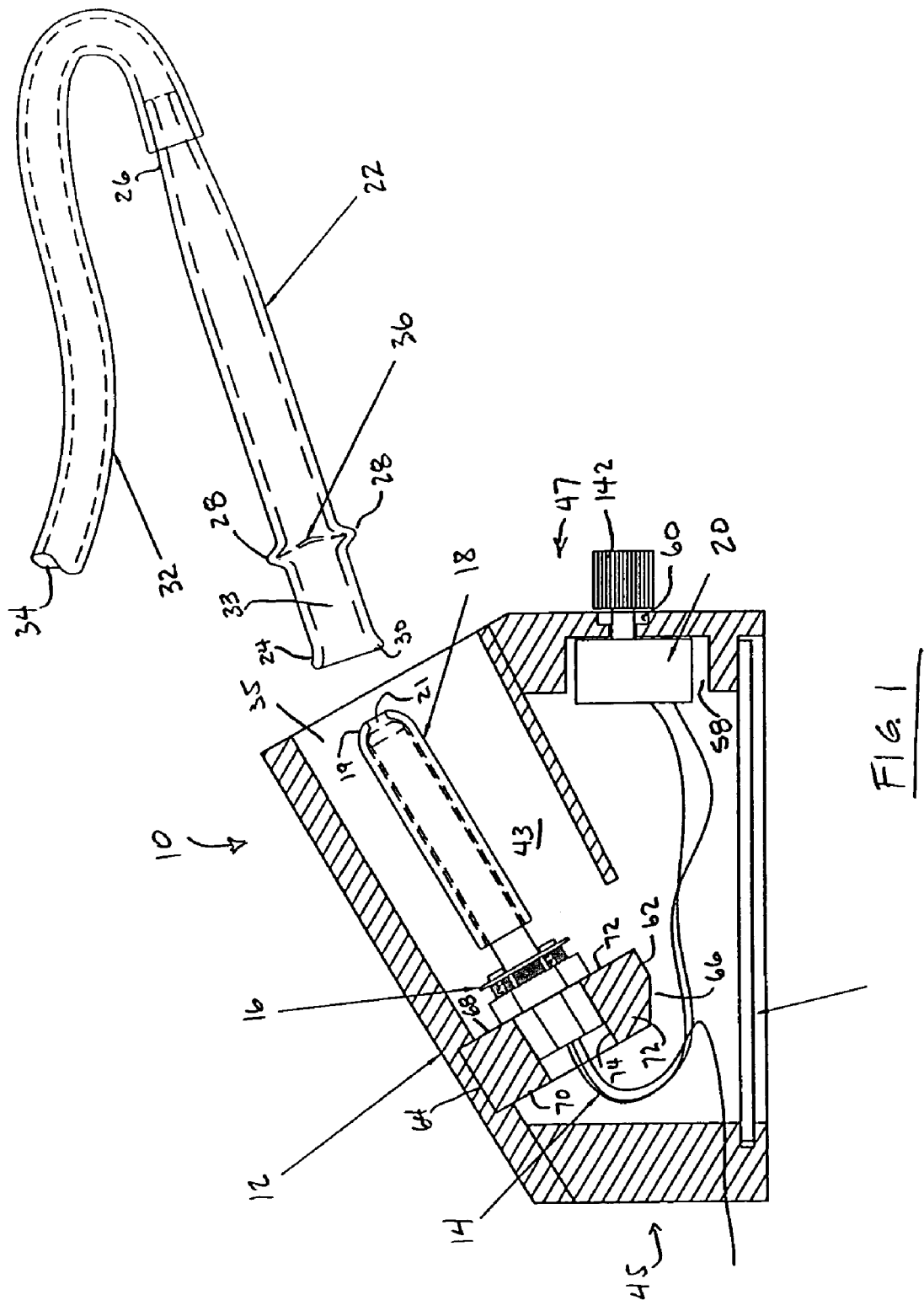
Figure 1A:
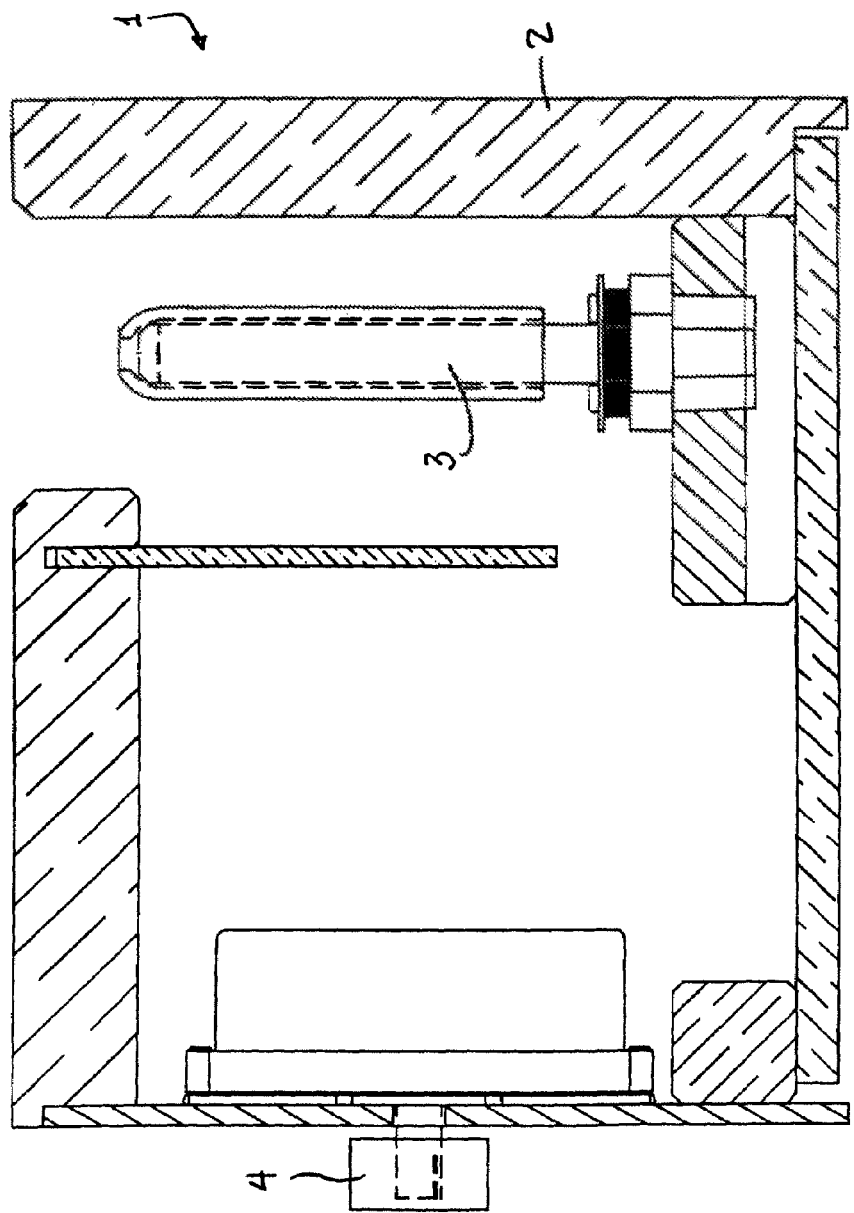
FIG. 1a is a semi-schematic cross-sectional view of a prior art vaporizer device.

Turning now to FIG. 1, there is shown an exemplary embodiment of a vaporizer apparatus provided in accordance with practice of the present invention, which is generally designated 10. The vaporizer apparatus 10 shown includes an enclosure 12 for housing a wire assembly 14, a heating element assembly 16, a shield 18, and a dimmer assembly or power regulator 20. The vaporizer apparatus 10 is preferably used with a hand piece 22 by placing the hand piece adjacent the shield 18 until they contact and then holding the hand piece in the contacted position during inhalation so that air may transfer from the vaporizer apparatus 10 through to the hand piece and then on through to the user, as further discussed below. The shield 18 comprises a tapered end 19, which has an opening 21 to allow the passing of the intake or draw air.

The hand piece 22 preferably comprises a glass pipe or tube that is commercially available from Pyrex, or its equivalence. The hand piece 22 has an inlet end 24 and an outlet end 26 and a groove 28 disposed thereinbetween, preferably near the inlet end. The inlet end 24 includes a flared or tapered section 30 that is dimensioned to mate with the cone section of the shield, and the outlet end 26 is preferably tapered along the longitudinal axis of the hand piece 22 to a dimension that is smaller relative to the inlet end for connecting to a flexible tube or extension member 32. The flexible tube 32 utilized in the present embodiment is preferably a commercially available clear vinyl or plastic tubing, which may optionally be opaque or semi-opaque. The flexible tubing 32 is connected on one end to the outlet end 26 of the hand piece 22 and is open on the other end, the draw end 34, for inhalation. Optionally, the hand piece 22 may be used without the flexible tubing 32.

A screen 36, which is made of a small wire meshed material is fitted within the groove 28 of the hand piece 22 by pushing the screen from the inlet end 24 until the outer perimeter of the screen wedges within the space provided by the groove. In one embodiment, the screen 36 is made from a stainless steel mesh. However, any variety of small meshed materials may be utilized in the present embodiment provided they are (1) sufficiently small to capture certain sized suspended materials and air borne ash present in the smoke, and (2) are capable of withstanding the temperature of the smoke. The screen 36 may be replaced by using a wooden skewer stick, or a similar tool, to push and dislodge the screen from the groove 28 out of the inlet end 24. Once the used screen is removed, a new fine meshed screen may be inserted and seated in the groove 28. The vaporizing chamber 33 is located in between the screen 36 and the inlet end 24, where herbs are packed for vaporizing.

Figure 2:
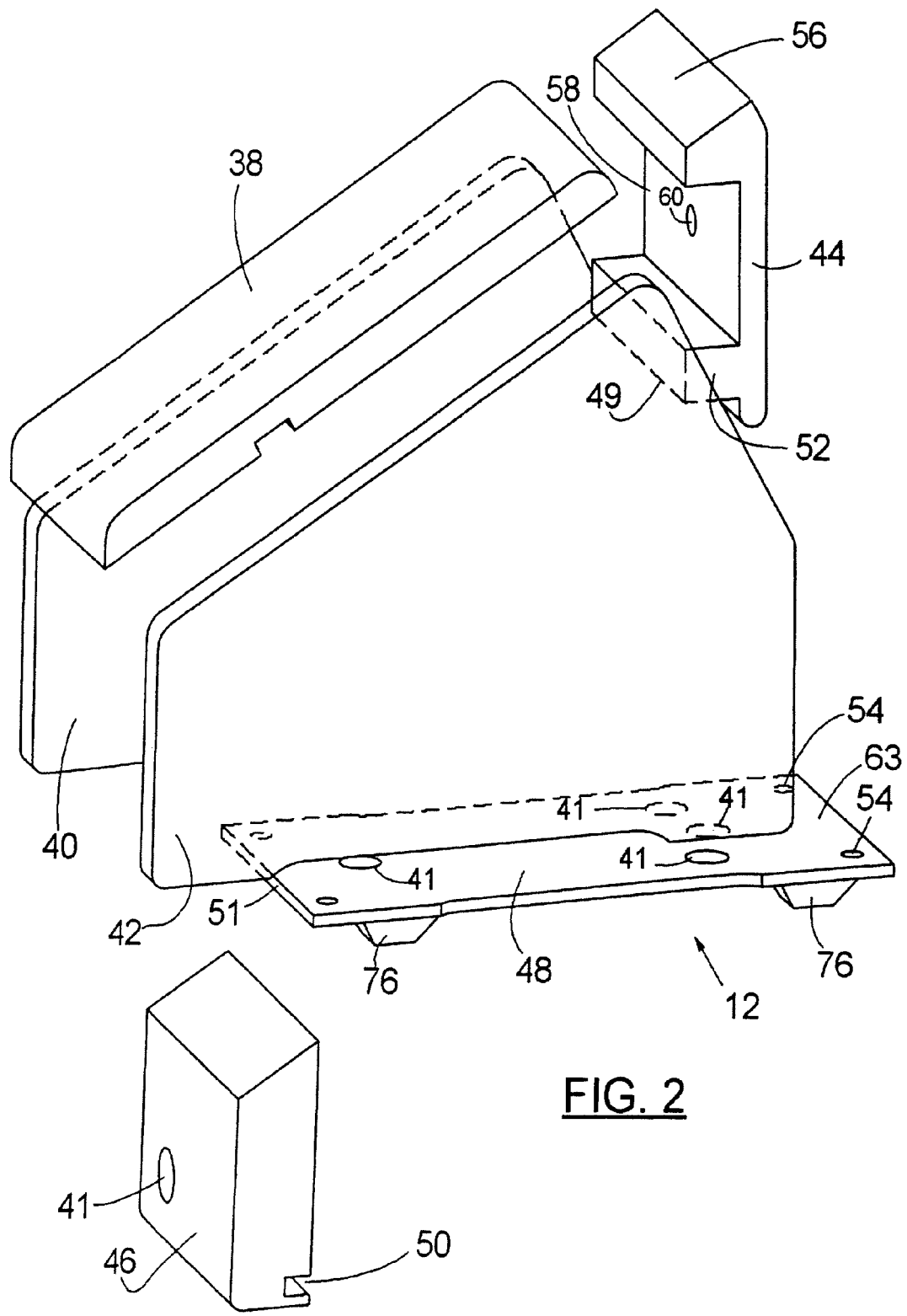
FIG. 2 is a semi-schematic exploded view of the enclosure of the vaporizer apparatus according to one embodiment of the invention.

FIG. 2 is a semi-schematic exploded perspective view of the enclosure 12 provided in accordance to one embodiment of the invention. As shown in FIG. 2, the enclosure 12 is assembled from a plurality of individual panels, which in the present embodiment includes wood and plastic panels. The enclosure 12 comprises an upper panel 38, two side panels 40, 42, a face panel 44, an end panel 46, which are preferably made from birch wood, and a bottom panel 48, which is preferably made from plastic and which has an opening 41 for ventilation. However, the number of individual panels and the material type can vary depending on the shape and modifications desired by a person skilled in the art. In addition, other openings may be incorporated in the other panels to permit even greater circulation within the enclosure 12.

To assemble the enclosure 12, the upper 38, side 40, 42, face 44, and end 46 panels are glued, nailed, and/or fastened to one another along their edges. Together, these components form the upper enclosure housing. When so formed, the upper enclosure housing defines a central cavity 43, a backside 45, and a front side 47 (FIG. 1).

To attach the plastic bottom panel 48 to the upper enclosure housing, a slot or channel 50 is machined into the end panel 46, along the lower side of the surface that faces into the interior of the upper enclosure housing 12. The slot 50 is configured to receive a first edge 51 of the bottom panel 48. As for the second edge 63 of the bottom panel 48, holes are provided along the underside 49 of the lower ledge 52 of the face panel 44 to threadedly receive a pair of screws or fasteners (not shown). Holes 54 are also provided near the second edge 53 of the bottom panel 48. Thus, once the upper enclosure housing is formed, the bottom panel 48 may be assembled to the upper enclosure housing by sliding the first edge 51 into the slot 50 located on the end panel 46 and then threading a pair of screws through the hold-down holes 54 and into the underside 49 of the lower ledge 52 of the face panel 44.

Referring again to FIG. 1 in addition to FIG. 2, the enclosure 12 supports the heating element assembly 16 and the wire assembly 14, and holds the dimmer assembly 20 in place along the face panel 44. More particularly, the face panel 44 includes an upper ledge 56 in addition to the lower ledge 52 and a mounting channel 58 defined thereinbetween. The mounting channel 58 is configured to receive the dimmer assembly 20 and includes an opening 60 for allowing the control arm on the dimmer assembly 20 to protrude therethrough. As further discussed below, the control arm allows the user to control the amount of heat generated by the heating element assembly 16.

To support the heating element assembly 16, a support plate 62 is used (FIG. 1). The support plate 62 has a top surface 64, a bottom surface 66, a front surface 68, a back surface 70, and two side surfaces 72. The support plate 62 may be mounted to the upper enclosure housing by nailing, fastening, and/or gluing the top surface 64 to the upper panel 38 and the two side surfaces 72 to the two side panels 40, 42. Optionally, the upper panel 38 may include a slot and the support plate 62 received in the slot for registering the location of the support plate with respect to the front side of the vaporizer apparatus 10. The support plate 62 is configured to support the heating element 16 by providing an opening 74 through which the heating element 16 can be secured thereto.

For viewing the heating element assembly 16 for color, such as a bright orange or a dull red, to determine whether the device is ready for use and having conveniently placed power regulator 20 for controlling the heating element assembly, the heating element assembly is preferably mounted at angle close to the opening 35 of the enclosure 12 (FIG. 1). In addition, by mounting the heating element assembly 16 at an angle and close to the opening 35, the vaporization device 10 is more ergonomic than the prior art device 1 (FIG. 1) as it is easier for the user to connect the hand piece 22 from the side than from the top, where his or her view may be obstructed. Preferably, the angle is between 25° to 90° from vertical, with 45° to 60° being more preferred. Vertical can be assumed to be the orientation of the prior art heating element 3 (FIG. 1).

Alternatively, the present invention may be practiced without tilting the hand piece 22 to mate with the shield 18, which places the inlet end 24 below the outlet end 26 as shown in FIG. 1. For example, the vaporizer apparatus 10 may be inverted so that the hand piece 22 is mated to the shield 18 when moved from a lower position to a higher position. When so practiced, the inlet end 24 of the hand piece 22 will be higher than the outlet end 26 (this may be visualized by turning FIG. 1 a half-circle rotation, i.e., 180°). One advantage to implementing this change is the ability to eliminate the packed essences in the hand piece 22 from falling out of the inlet end 24 during usage. Accordingly, the mounting angle of the heating element assembly 16 may also be 91° to 180° from vertical, with 110° to 180° being more preferred.

It is understood that when the mounting angle of the heating element 18 is varied (such as discussed above), variations in the placement of the dimmer assembly 20 and the configuration of the enclosure 12 may also vary to provide the user with easy access to both the dimmer assembly and the heating element assembly. Accordingly, all such changes are contemplated to fall within the scope of the present invention.

As readily apparent, the bottom panel 48 is removable for easy access to the central cavity 43 of the upper enclosure housing. This is desirable where maintenance is contemplated, such as for changing the wiring, for replacing the heating element assembly, etc. Referring again to FIG. 2, the bottom panel 48 may include integrally molded support legs 76 for elevating the enclosure 12 from a support surface, such as a table or a counter top. If the bottom panel 48 is instead made from wood, rubber stops or cushions may used to provide the same elevation function as the support legs 76.

Figure 3:
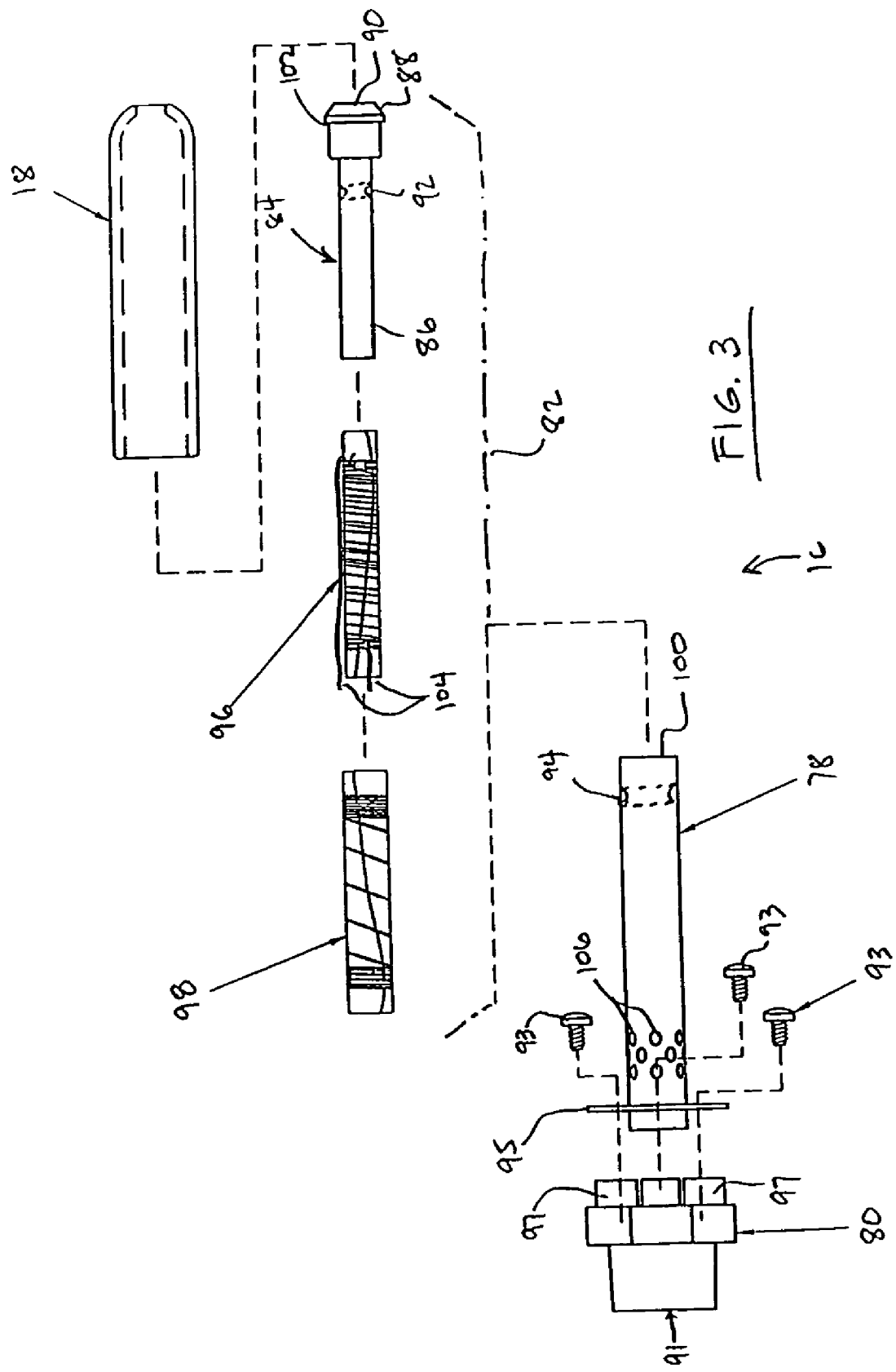

FIG. 3 is an exploded view of the heating element assembly 16. The heating element assembly 16, as shown in FIGS. 1 and 3, is a modified version of a heating coil commonly incorporated in a 30-watt soldering iron, which is commercially available from a variety of retailers. One such retailer is CVF Supply Company at www.cvfsupplycompany.com.

U.S. Pat. No. 5,031,817 to Chen and U.S. Pat. No. 4,766,289 to Santoro et al., the contents of which are expressly incorporated herein by reference, describe the principles and operations of soldering irons. Thus, further discussion is not believed necessary.

In one embodiment, the heating element assembly 16 includes a base 80 and an inner core assembly 82 disposed within an outer steel casing 78. The inner core assembly 82 includes an inner steel core 84 having a cylindrical shank 86 connected to a cylindrical head 88. The inner steel core 84 defining a passage or annular opening 90 for air flow to flow through during a draw or inhalation by the user. Similarly, the base 80 includes a passage 91 that aligns with the annular opening 90 of the inner steel core 84 for air flow to flow through, as further discussed below.

The cylindrical shank 86 includes a threaded groove 92 for receiving a set screw, which is positioned in a corresponding spatial relationship as the threaded groove 94 located on the outer steel casing 78. A heating coil assembly 96 wrapped around by an outer insulating assembly 98 is then mounted over the shank 86 of the inner steel core 84, which together makes up the inner core assembly 82. The inner core assembly 82 as described is similar to a commercially available 30-watt soldering iron.

The inner core assembly 82 is then positioned into the outer steel casing 78 by sliding the inner core into the distal end 100 until the neck section 102 on the cylinder head 88 abuts the distal end of the steel casing. The inner core assembly 82 is then secured to the outer steel casing 78 by inserting a set screw (not shown) through the opening 94 located on the outer steel casing. The outer steel casing 78 and the inner core assembly 82 are then mounted onto the base 80 with the wire leads 104 on the heating coil assembly 96 connected according to the electrical diagram shown in FIG. 8, and described further below. Fastening one or more screws 93 through the flange 95 and then to the threaded receptacles 97 located on the base will secure the two components together. The base is preferably made from a phenolic material but may optionally be made from any high temperature resistance material such as fiberglass and ceramic.

The outer steel casing 78 has a plurality of ports 106 distributed on the surface of the steel casing to function as air inlets for cooling the heating coil assembly 96. The described heating element assembly 16 is then mounted onto the support plate 62, which is then mounted to the central cavity 43 of the enclosure 12 in the manner previously discussed. The shield 18 is then placed over the heating element assembly 16 to shield the same from direct contact therewith. Although the heating element assembly 16 is described with particularity, it is understood that other heating element assemblies may be used, such as a ceramic heating assembly, which may be found in home space heaters.

In the present embodiment, the shield 18 acts to minimize heat loss from the heating element assembly 16 and to insulate the enclosure 12, among others. Thus, other shielding or insulation means may be used instead of or in addition to the glass shield 18 to provide the stated functions. For example, fiberglass insulating material may be wrapped around the shield 18 while leaving the mating section or tapered end 19 of the shield exposed for mating with the hand piece 22. When so implemented with the additional insulation, the enclosure 12 may be modified to take on a smaller contour relative to the heating element assembly 16 to provide for an overall more compact vaporizer apparatus 10.

Figure 4:
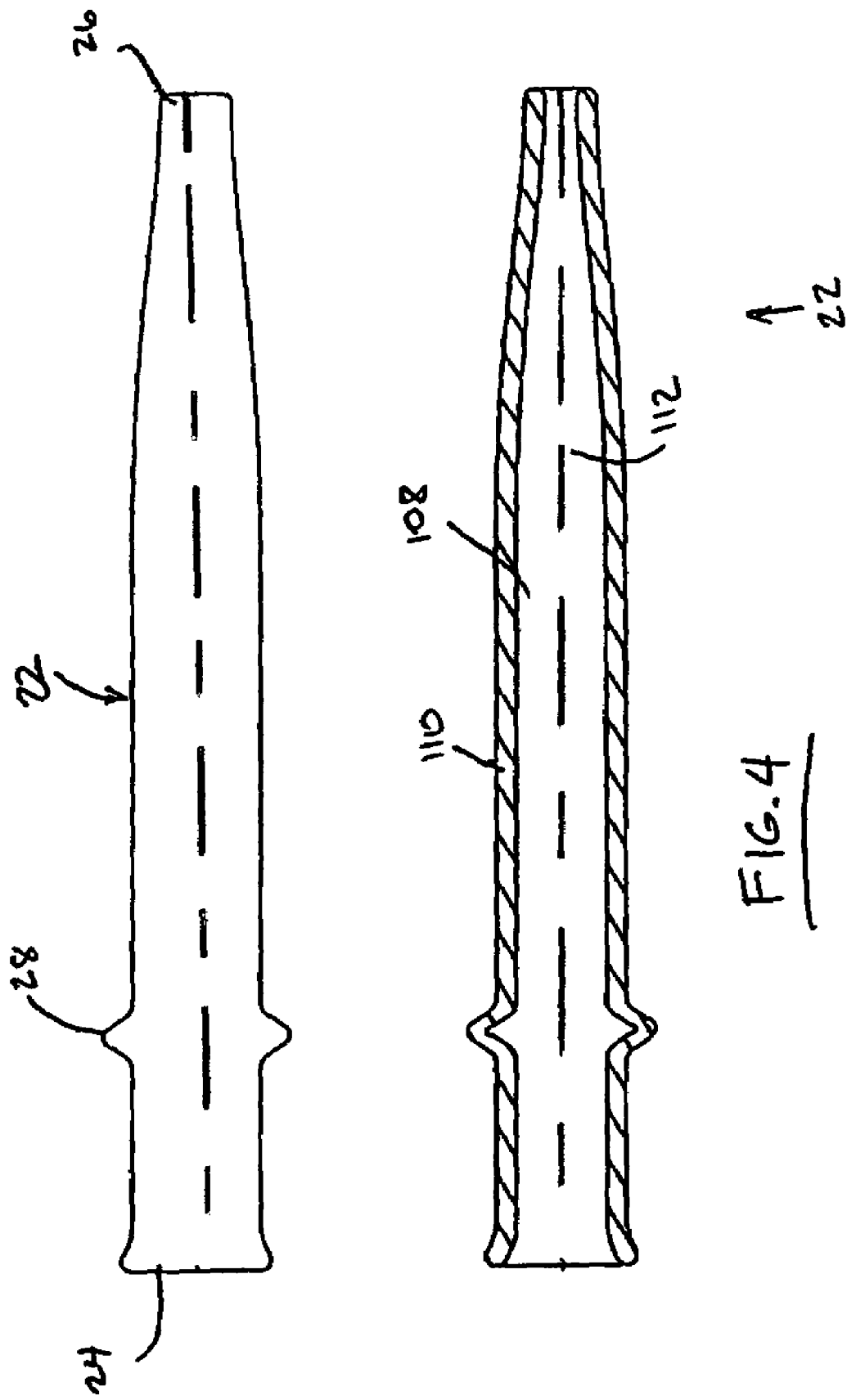
FIG. 4 is a semi-schematic cross sectional view of a hand piece abutting the heating element.

FIG. 4 is a combination plan view and cross-section view of the hand piece 22 for mating with the shield 18 located on the heating element assembly 16. As previously discussed, the hand piece 22 comprises an inlet end 24, and outlet end 26, and a groove 28 disposed thereinbetween. As shown, the inlet end includes an outward radius or tapered section 30 that matches the opening 21 of the shield 18, an inner surface 108 that forms an enclosure for the intake air, an outer surface 110 for gripping, and a longitudinal axis 112. Exemplary dimensions include an overall length of 5-8 inches, largest diameter cross-section of 0.65-1.0 inch, and glass thickness of 0.0625-0.125 inch. However, other dimensions may be used with equal effectiveness and are contemplated to fall within the scope of the present invention.

Figure 5:
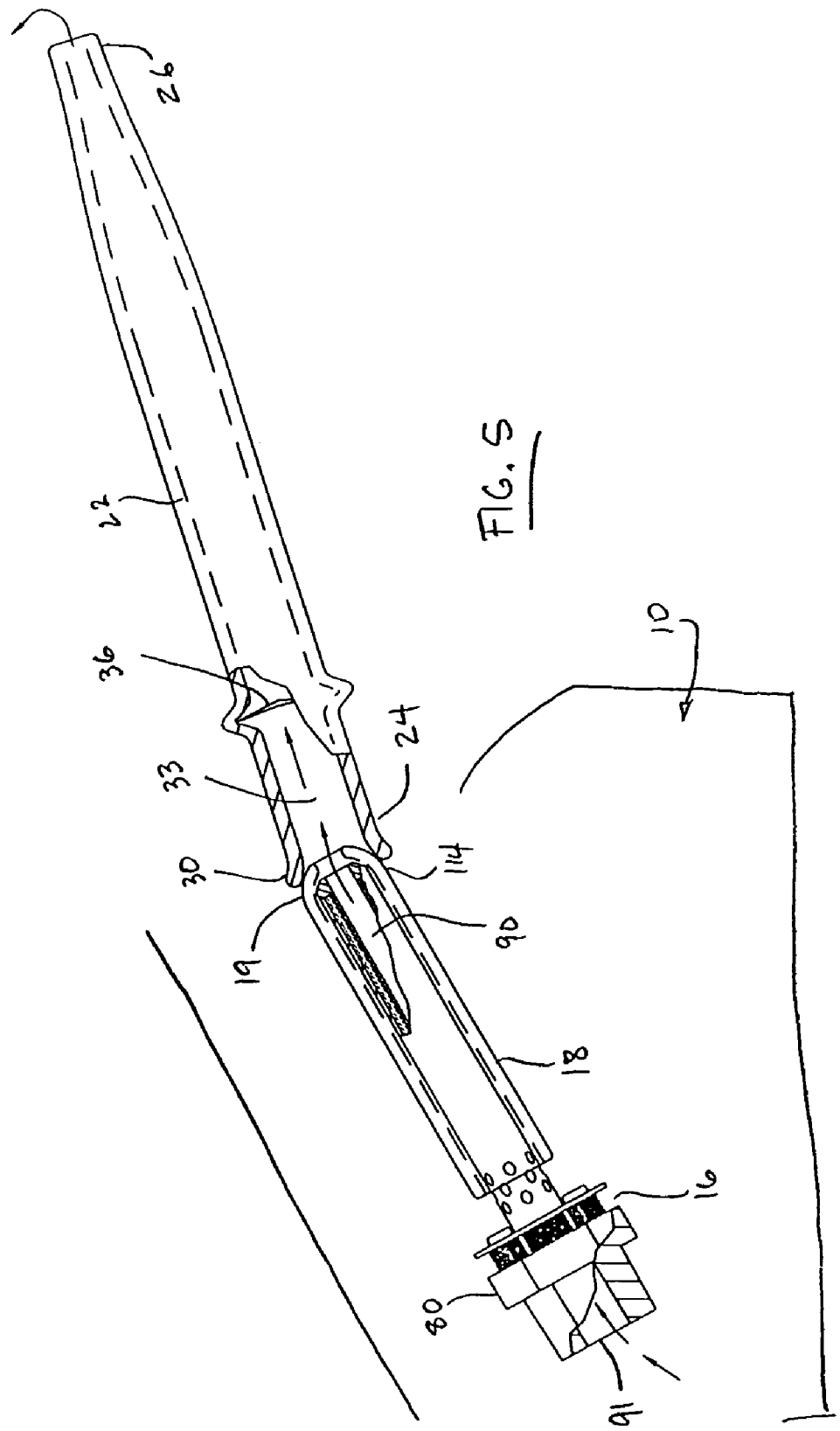
FIG. 5 is a combination semi-schematic side view and cross-sectional view of the hand piece in use with the vaporizer apparatus.

FIG. 5 depicts the manner in which the hand piece 22 is utilized with the vaporizer apparatus 10. FIG. 5 specifically illustrates the placement of the hand piece 22 to the distal end of the shield 18 to provide a flow path from between heating element assembly 16 and the hand piece. As shown, the tapered end 30 of the hand piece 22 is in contact with the distal end 114 of the shield 18, which has a semi-closed end or dome 19 having an opening centrally located thereon for air flow. The semi-closed end or dome 19 preferably has a curvature that corresponds to the outward radius 30 of the inlet end 24 of the hand piece such that when the outward radius or tapered end 30 abuts with the semi-closed end 116, a sufficiently tight seal is formed which is capable of sealing the interface between the two from excessive or unwanted leakage.

In use, the apparatus 10 is first plugged into an electrical socket and the dimmer assembly 20 is turned to adjust the input power to the heating element assembly 16, i.e., the apparatus is heated to the correct temperature. Herbs or carriers are then packed into the hand piece 22 and the hand piece is then connected to the shield 18, which is placed over the heating element assembly 16. Negative pressure is then generated at the outlet end 26 of the hand piece 22, or at the draw end 34 of a flexible tubing 32 if one is connected to the hand piece, by a user. A corresponding negative pressure is generated at the opening 91 located on the base unit 80. Negative pressure causes air to flow through the opening 91 and then through the annular passage 90 of the inner steel core 84 where it finally exits the semi-closed end 116 located on the shield 18.

When air travels through the annular passage 90 of the inner steel core 84, air is heated by the inner steel core via conduction, convection, and radiation heat generated by the heating element assembly 16. The amount of air temperature rise depends in part on the dimmer assembly 20 setting, as further discussed below, and the amount of negative pressure generated by the user at the outlet end 26, which determines the air volume and velocity as air travels through the annular passage 90.

Accordingly, when herbs or carriers are packed within the vaporization chamber 33, which is defined by the space located in between the screen 36 and the inlet end 24 of the hand piece, dry heated air passes through the packed herbs and vaporizes the essences and aroma that are present in the herbs to produce smoke. The smoke is then mixed with the intake air and travels out of the outlet end 26, or draw end 34 if a flexible tubing 32 is used, and into the lungs of the user.

The amount or quality of essences extracted is dependent on the set point of the vaporizer, the volume of the airflow, and the properties of the herbs that is to be extracted out of the herbs. The apparatus may be modified to exchange and carry out multiple samples efficiently by adding additional vaporizing chambers. For example, a tee or several tees may be used with each branch of each tee having a hand piece mounted thereto and connected to the heating element assembly for concurrently serving multiple users.

Figure 6:
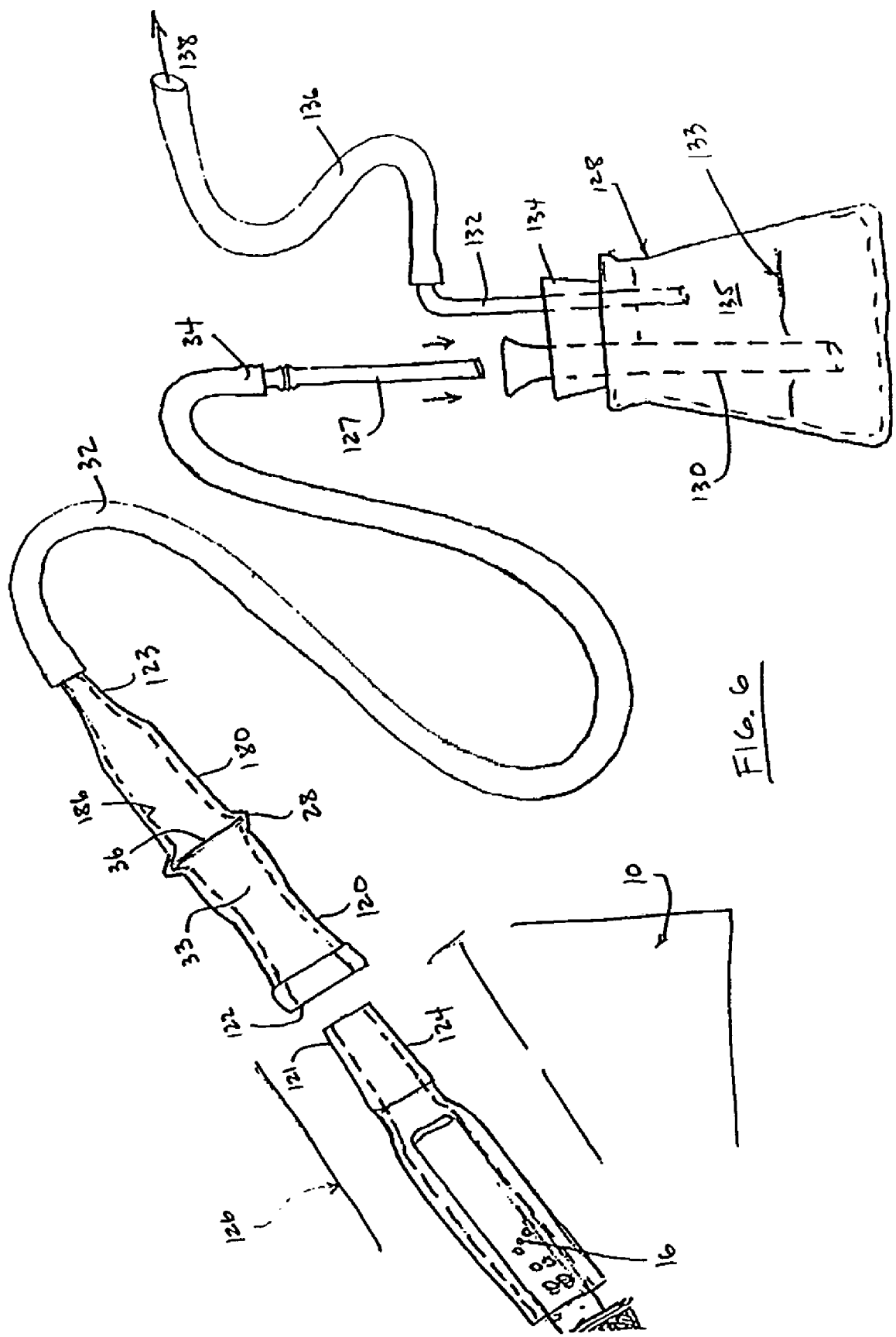
FIG. 6 is a semi-schematic perspective view of a modified shield and a modified hand piece of the vaporizer apparatus used in combination with a smoking device that has a water reservoir.

FIG. 6 shows an alternative application for the vaporizer apparatus 10 provided in accordance with practice of the present invention. Broadly speaking, the alternative application includes the use of a water medium for cooling the smoke before it enters the user's lungs. As shown, a modified hand piece 120 fabricated from a glass tube and having a screen 36 positioned within a groove 28 is used, which has a receiving end 122 and an outlet end 123. The receiving end 122 is configured to receive a portion of a modified shield 126 so that a portion of the shield fits inside the receiving end. This interaction between the receiving end 122 and the shield 126 produces a greater surface contact between the two components, and hence, a better seal than the embodiment shown in FIG. 1.

In particular, the shield 126 includes a tapered cone section 124, which is dimensioned such that it is capable of being inserted into the receiving end 122 of the hand piece 120 to form a suitably tight seal. The tapered cone comprises a small inlet diameter 121 that is sufficiently smaller than the diameter of the receiving end 122. These relative dimensions allow the receiving end 122 to easily fit over the tapered cone section 124 of the modified shield 126 to provide a seal without having to maneuver the two components until their respective curvatures match, such as that shown in FIG. 5. Thus, a more effective seal is provided between the connection point of the present invention relative to the connection point of the invention disclosed in FIGS. 1 and 5. It is understood that the shield 126 and the heating element assembly 16 are part of the vaporizer apparatus 10 described above, which has been eliminated for clarity purposes. For obvious reasons, a tighter seal is preferred, as there are more connections, lengths, and pressure drop from between the user and the vaporization chamber 33.

The water medium is contained with a flask container 128 and is filled to a pre-determined level, which is above the inlet end of a down stem 130. The space above the water level and the stopper 134 inside the flask container 128 is referred to as the vapor chamber 135. The flexible tube 32, which is connected to the outlet end 123 of the modified hand piece 120, is connected to one end of a first sample tube 127. A second sample tube 132 is positioned through the two-hole stopper 134, which has a first end disposed within the flask but above the water level 133 and a second end that is connected to a second flexible tube 136. As shown, the second flexible tube 136 has a free end or a draw end 138 that is configured for inhalation by a user.

Although not shown, the draw end 138 may be attached to a draw element, which has a shape that facilitates connection or attachment to the mouth of lips of the user. In addition, the invention may be practiced by eliminating the down stem 130 from the flask container 128 and inserting the first sample tube 127 directly into the two-hole stopper 134. Still alternatively, a conventional water-based smoking apparatus may be used instead of the flask container 128.

In use, the vaporizer assembly 10 is powered up by plugging the cord of the heating element assembly 16 into an electrical outlet. Herbs are then packed into the vaporizing chamber 33. The user then places the receiving end 122 over the tapered end 124 of the shield 126 and inhales. The user creates negative pressure by inhaling on the draw end 138. The inhalation creates a vacuum in the vapor chamber 135, which causes the water level to rise, which then causes a vacuum in the first flexible tubing 32. As previously discussed, the vacuum in the first flexible tubing causes air to flow through the opening 91 in the base 80 (not shown) and through the annular opening in the inner steel core 84 (not shown in FIG. 6 but shown in FIG. 3).

As air travels through the inner steel core 84, the inner steel core heats it. Heated air then travels through the vaporizing chamber 33 where it contacts with the packed herbs. The heat vaporizes some of the active ingredients present in the herbs, which release in the form of smoke. Smoke and heated air then travels through the flex tube 32 then through the water medium. The mixture of smoke and air is then cooled by the water medium as it rises through the water medium up to the vapor chamber 135. Cooled mixture of smoke and air then flows through the second tube sample 132 and the second flexible tube 136 where it exits the draw end 138 and into the lungs of the user. In addition to cooling the mixture of smoke and air, the water medium also filters air borne matters that may be carried with the smoke when the carriers are heated.

Figure 7:
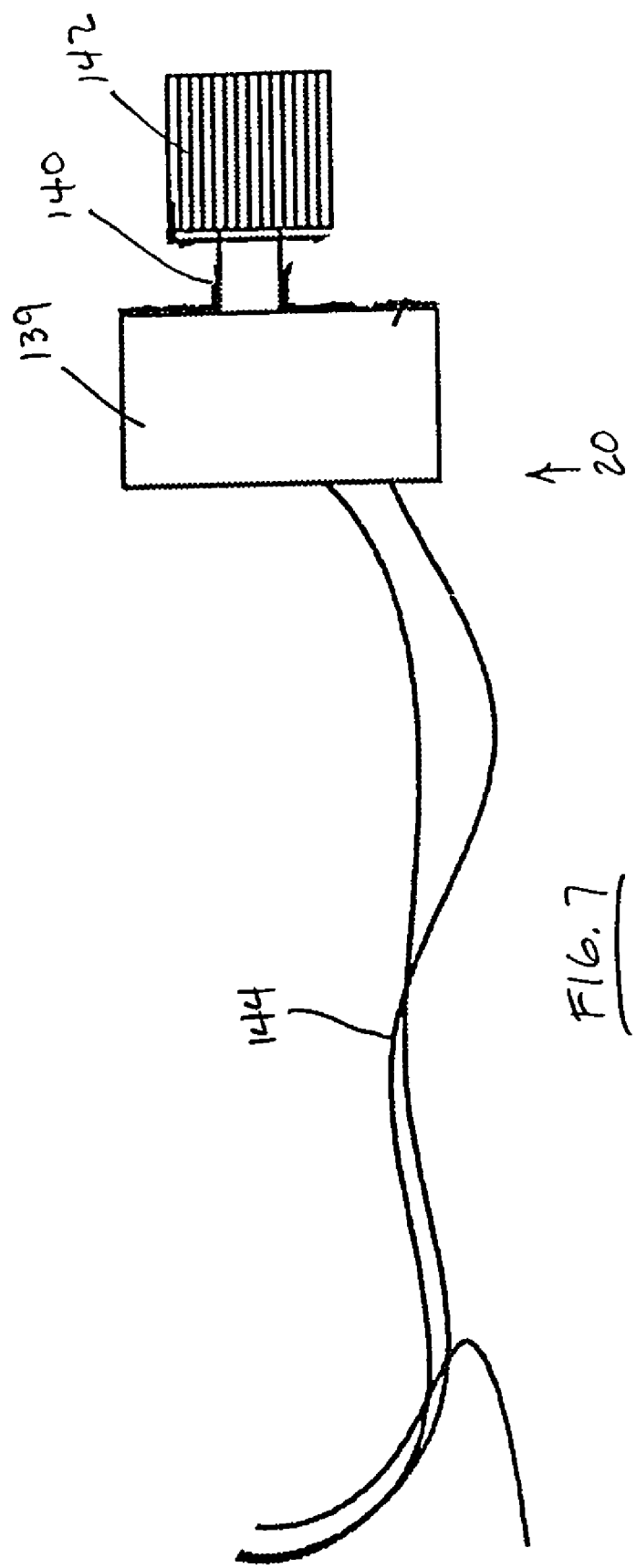
FIG. 7 is a semi-schematic perspective view of a power regulator of the vaporizer apparatus.

FIG. 7 is a semi-schematic side view of the dimmer assembly 20 provided in accordance to one embodiment of the invention. The dimmer assembly 20 is a commercially available full-range rotary manual dimmer switch, also commonly referred to as a rheostat 139. The dimmer assembly 20 includes a control arm 140 and a control knob 142 having a positive click "off" with extended semi-circular rotation for full range dimming control. The dimmer switch 20 has leads or wires 144 for connecting to an electrical source and mechanisms for locking the switch in the off position until positively turned to an "on" position. The knob 142 rotates to increase or decrease the intensity of the electric current thereby increasing or decreasing the intensity of heat emanating from the heating element assembly 16. Alternatively, other power regulators having control circuits such as a transistor type dimmer switch, commonly referred to as a TRIAC, may be used to more efficiently operate the heating element assembly 16.

Figure 8:
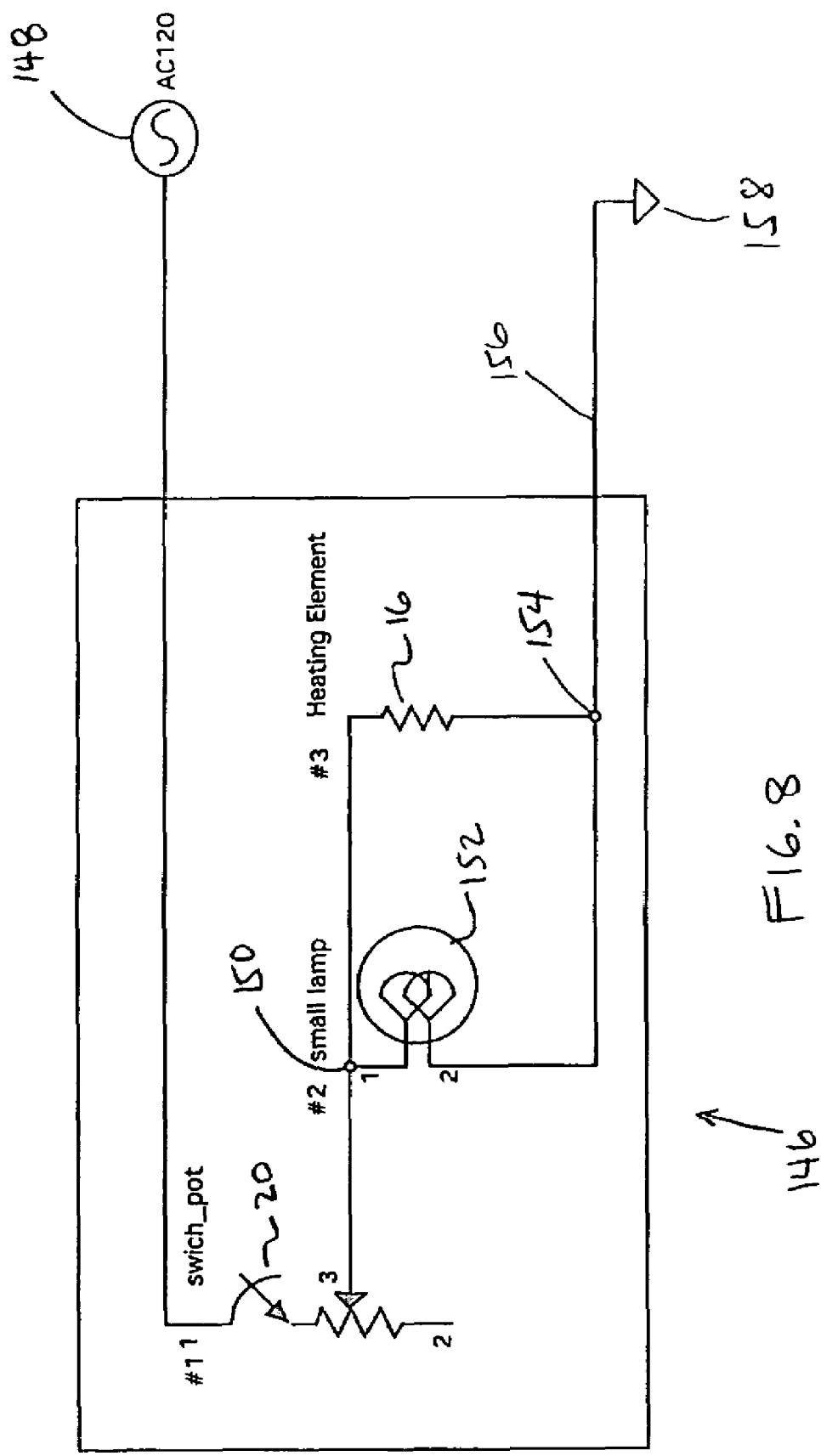
FIG. 8 is a schematic representation of an electrical circuit for the heating element assembly.

FIG. 8 is a schematic representation of the electrical wiring implemented in accordance with the present invention, generally designated 146. The electrical circuit 146 includes a power source 148, which is electrically connected in series to the full range dimmer switch 20. Connected to the dimmer switch 20 at node 150 are an optional lamp 152 and the heating element assembly 16. The lamp 152 and the heating element assembly 16 are connected at node 154, thus providing them with a parallel electrical configuration. The lamp 152, if included, may be placed in the central cavity 43 of the upper housing enclosure by loosely attaching it to the bottom panel 48. A lead 156 extending from the heating element assembly 16 is connected to a grounding lug 158 to ground the entire vaporizer assembly 10.

Figure 9:
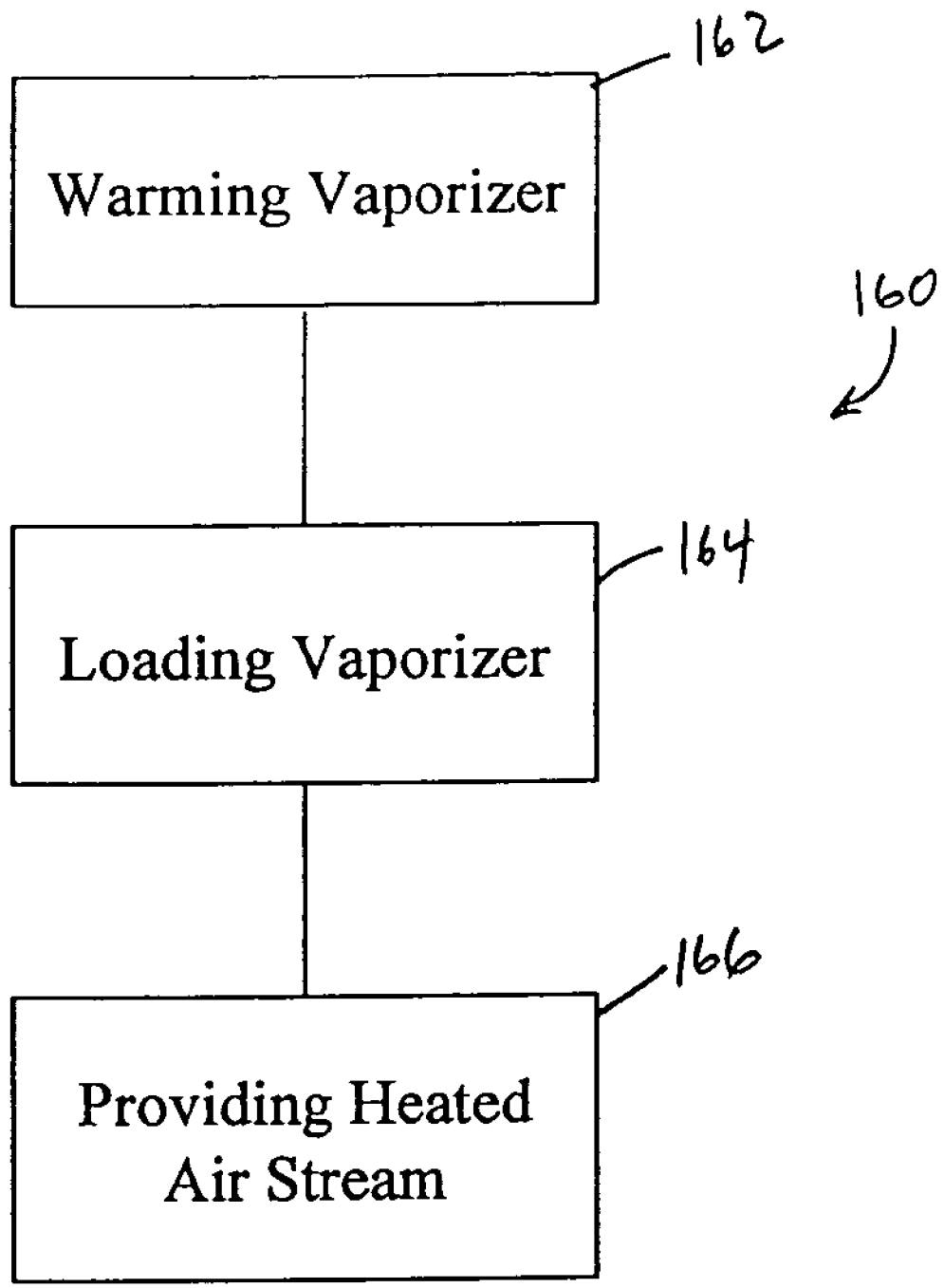
FIG. 9 depicts various method steps utilized in the operation of the vaporizer apparatus.

FIG. 9 depicts various method steps 160 utilized in the operation of the vaporizer apparatus 10 of the present invention. First, after plugging the assembly into an electrical outlet, the knob 142 on the dimmer assembly 20 is turned to the highest setting (i.e., maximum rotation) to allow the heating element assembly 16 to warm up at step 162, which is typically in the order of approximately 0 minutes. When the inside of the heating element assembly 16 becomes bright orange, the knob 142 is turned down in the off direction a little less than a quarter turn. Concurrently, before, of after, the vaporization chamber 33 (shown in FIGS. 1 and 4-6) of the hand piece 22 is loaded 164 with herbs. The herbs are either grounded or fluffed up to maximize surface contact with the heated air that is to be drawn in, which in turn ensures greater vaporization of the active ingredients. The user loads sufficient herbs to cover the screen, but preferably no more than approximately one-third of the vaporization chamber 33. Excessive force in packing the herbs in the vaporization chamber is not recommended as that may dislodge the screen 36 out from the groove 28 of the hand piece 22.

The user then places the inlet end 24, 122 over the end of the shield 18, 126, which is positioned over the heating element assembly 16. The user initially observes the color of the heating element assembly 16. If the color is bright orange, the user then draws in air quickly 166 to keep the heating element assembly 16 cool. Rapid inhalation also minimizes the likelihood that the herbs will ignite, as heat will not have sufficient time to build up. If the color is a dull red, then the user inhales naturally, similar to normal breathing. Thus, it may be beneficial to mark the control knob 142 on the dimmer assembly 20 after the desirable setting has been established. Inhalation by the user causes heated air stream to pass through the botanical specimen present in the vaporization chamber 33, which in turn extracts and transfers active ingredients to the user.

The user inhales steadily but fast enough to hear a subtle whistling sound in the hand piece 22, 120. If the contents of the vaporization chamber 33 accidentally ignite during the inhalation process, the user should immediately stop inhaling, removes the hand piece 22, 120 from the shield 22, and blows the hand piece 22 clean. This situation can also be remedied by inhaling faster and/or decreasing the setting on the vaporizer apparatus 10 and waiting a few minutes for the heating element assembly 16 to cool. To cool the heating element assembly 20 faster, the user can blow through the hand piece, which then directs cool air into the glass shield 18, 126.

Figure 10:
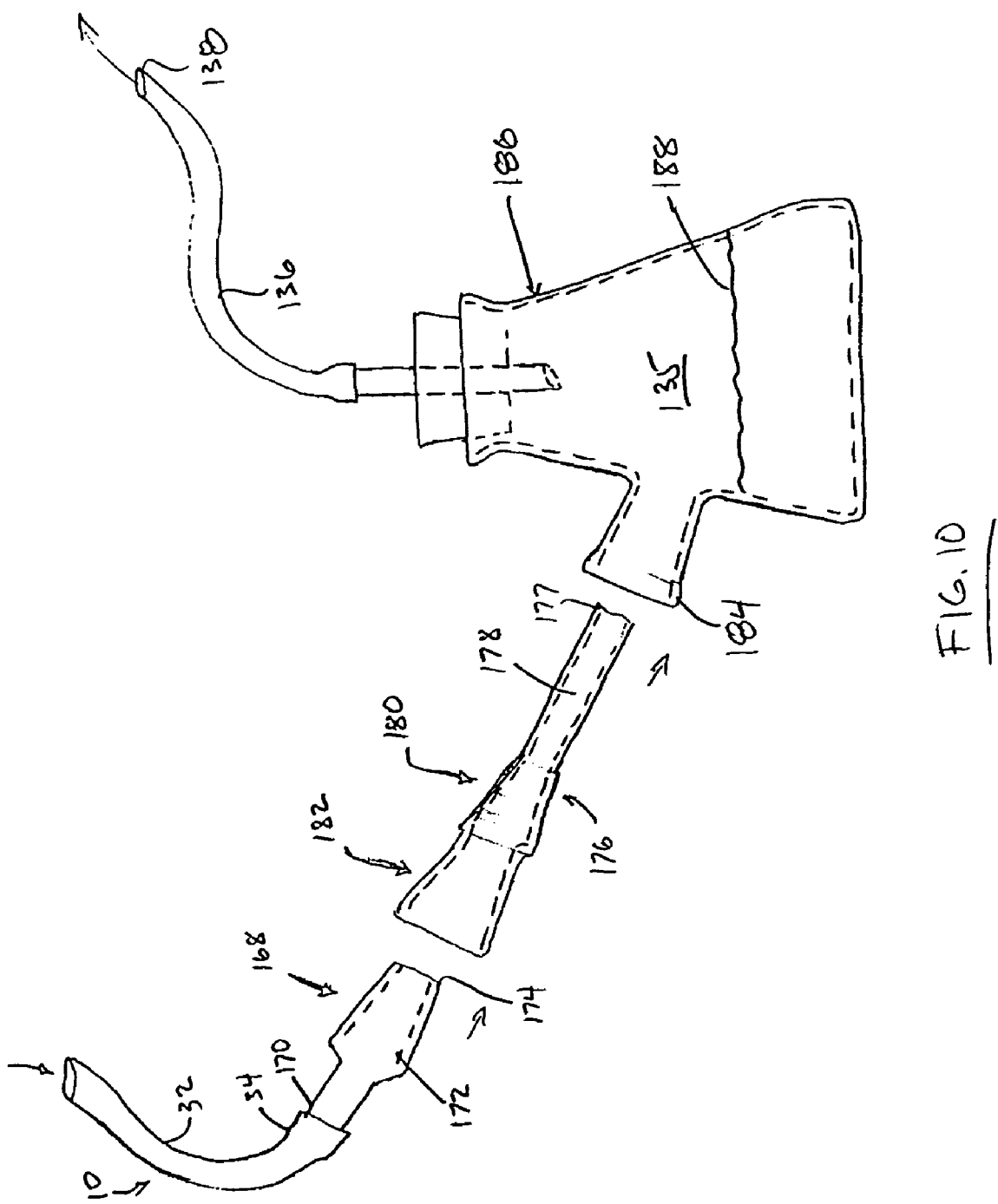
FIG. 10 is another semi-schematic perspective view of a modified shield and a modified hand piece of the vaporizer apparatus used in combination with a smoking device that has a water reservoir.

FIG. 10 shows yet another alternative application for the vaporizer apparatus 10 provided in accordance with practice of the present invention. As shown, the draw end 34 of the flex tube 32 is connected to an inhalation mouthpiece 168. The inhalation mouthpiece 168 comprises a connecting end 170, a dome-shape chamber 172, and a draw end 174 and is preferably made from glass. The draw end 174 is configured to mate with a modified down stem 176, which has a stem section 178, a first mating section 180 and a second mating section 182. The down stem 176 is preferably made from glass. However, other materials including aluminum and stainless steel may also be used without deviating from the scope of the present invention.

The stem section 178 of the down stem 176 is inserted into an inlet 184 of a water reservoir of flask 186 having a certain water level 188. However, other structures including a conventional water-based smoking apparatus may also be used instead of the flask. The lower end section 177 of the stem section 178 is inserted into the inlet 184 until the first mating section 180 of the down stem 176 makes contact and forms a seal with the inlet 184, via a tight fitting fit. Preferably when the seal is formed, the end section 177 of the stem section 178 is elevated from the base 190 of the water reservoir 186 and the water level 188 is above the end section.

The second mating section 182 of the down stem 176 is configured to mate with the draw end 174 of the inhalation mouth piece 168 when the same is inserted into the down stem. The mating between the inhalation mouthpiece 168 and the second mating section 182 preferably forms a seal, via a tight fitting fit. The seal formed between the second mating section 182 and mouth piece 168 and the seal formed between the first mating section 182 and the inlet 184 of the water reservoir 186 are preferably such that when air is inhaled from the draw end 138 of the second flexible tube 136, a vacuum is maintained within the vapor chamber 135 of the water reservoir 186.

Figure 11:
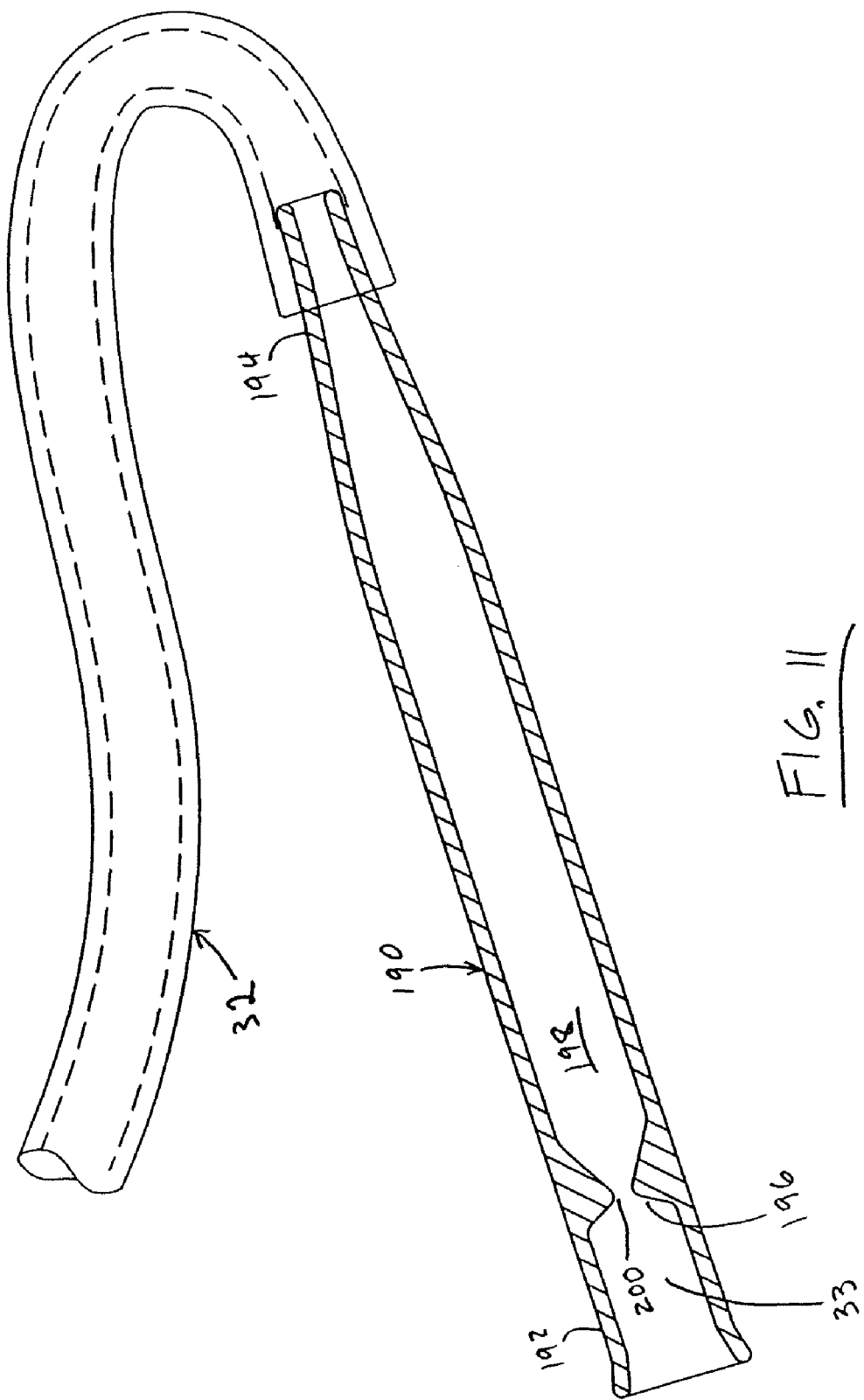
FIG. 11 is a semi-schematic cross-sectional view of an alternative hand piece provided in accordance with practice of the present invention.

FIG. 11 depicts an alternative hand piece 190 provided in accordance with practice of the present invention. The hand piece 190 comprises an inlet end 192, an outlet end 194, and a bottleneck section 196 located within the axial bore 198 of the hand piece 190. The bottleneck section 196 comprises an opening 200 for allowing the inlet end 192 to communicate with the outlet end 194. Just distal of the opening 200 in the direction of the inlet end 192 is the vaporization chamber. The opening 200 is preferably in the order of about 0.05 to 0.3 inch to minimize seepage or passage of the packed herbs in the vaporization chamber 33 from passing through the opening during use. Preferably, the opening is in the range of about 0.1 to 0.15 inch. Generally speaking, the bottleneck section 196 is a reduced section of the axial bore 198 to provide an area for packing the herbs and for minimizing passage of the packed herbs. The hand piece 190 is connected to a flexible tubing 32 and is useable in the same manner as previously discussed hand pieces, such as the hand piece 22 shown in FIG. 1.

Figure 12:
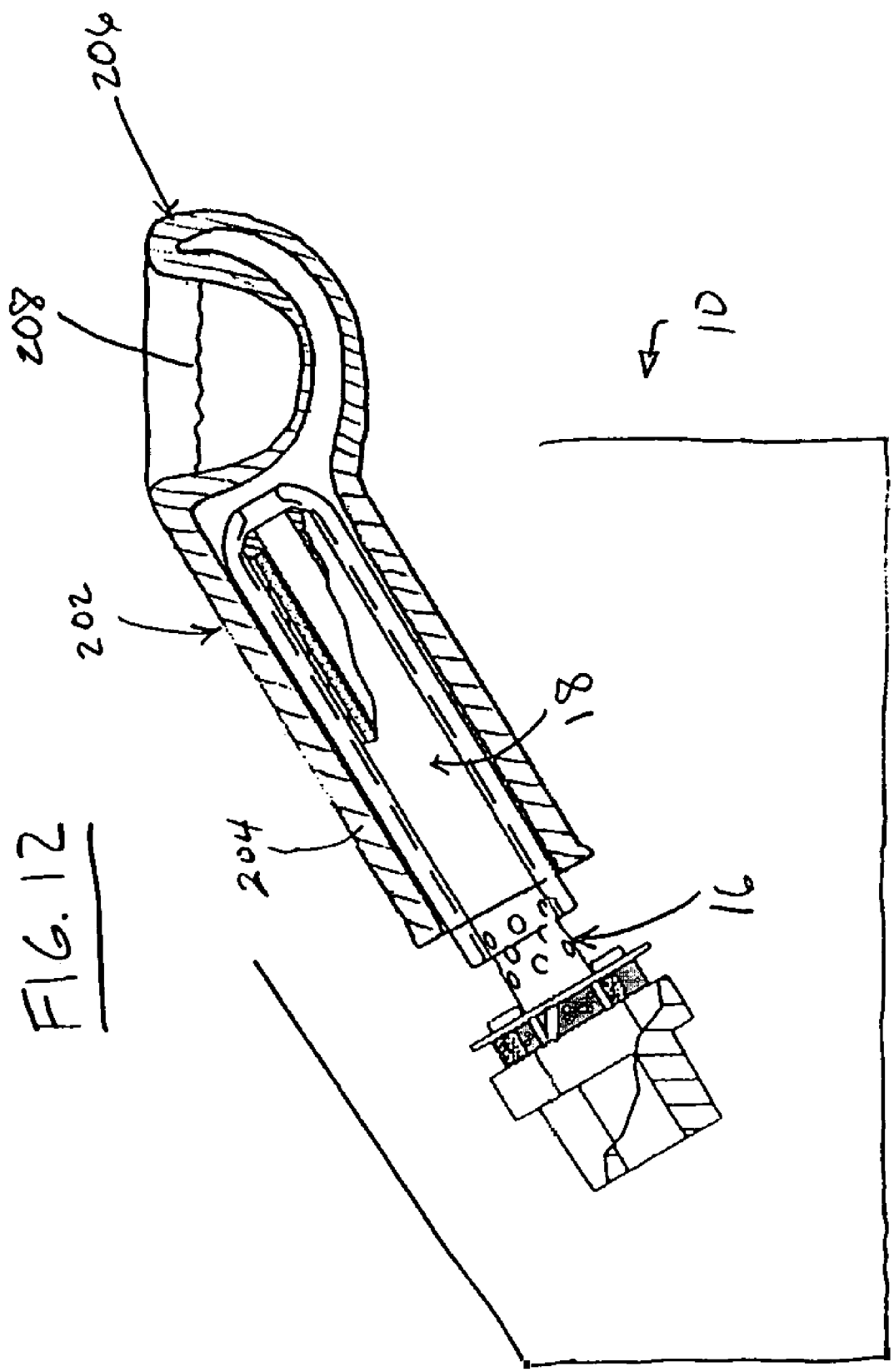
FIG. 12 is a semi-schematic cross-sectional view of the vaporizer apparatus being used in combination with an aroma therapy attachment.

FIG. 12 shows the vaporizer apparatus 10 provided in accordance with practice of the present invention in used with an aromatherapy attachment device 202. The attachment device 202 shown includes a body section 204 for receiving the shield 18, which is positioned over the heating element assembly 16, and a containment section 206, which in the present embodiment is in the shape of a bowl. The attachment device 202 is preferably made from glass, but other readily heat conducting materials may be used without deviating from the scope of the present embodiment, such as aluminum. The containment section 206 is configured to hold essential fluids 208, such as a combination of essential oil and water, for aromatherapy.

The combination vaporizer apparatus 10 and attachment device 202 is used by energizing the heating element assembly 16 as earlier discussed. The attachment device 202 is then slipped over the heating element assembly 16, or over the shield 18, if the shield is used. Essential fluid 208 is then added to the bowl section 206 of the attachment device to a desired level. Through conduction, convection, and radiation heat generated by the heating element assembly 16, the essential fluid 208 is heated. Preferably the essential fluid 208 is heated to well-below its boiling point, and more preferably to a warm touch so that essential vapor slowly releases from the essential fluid 208 to fill the surrounding space with herbal essences for inhalation by occupants of the surrounding space.

Figure 13:
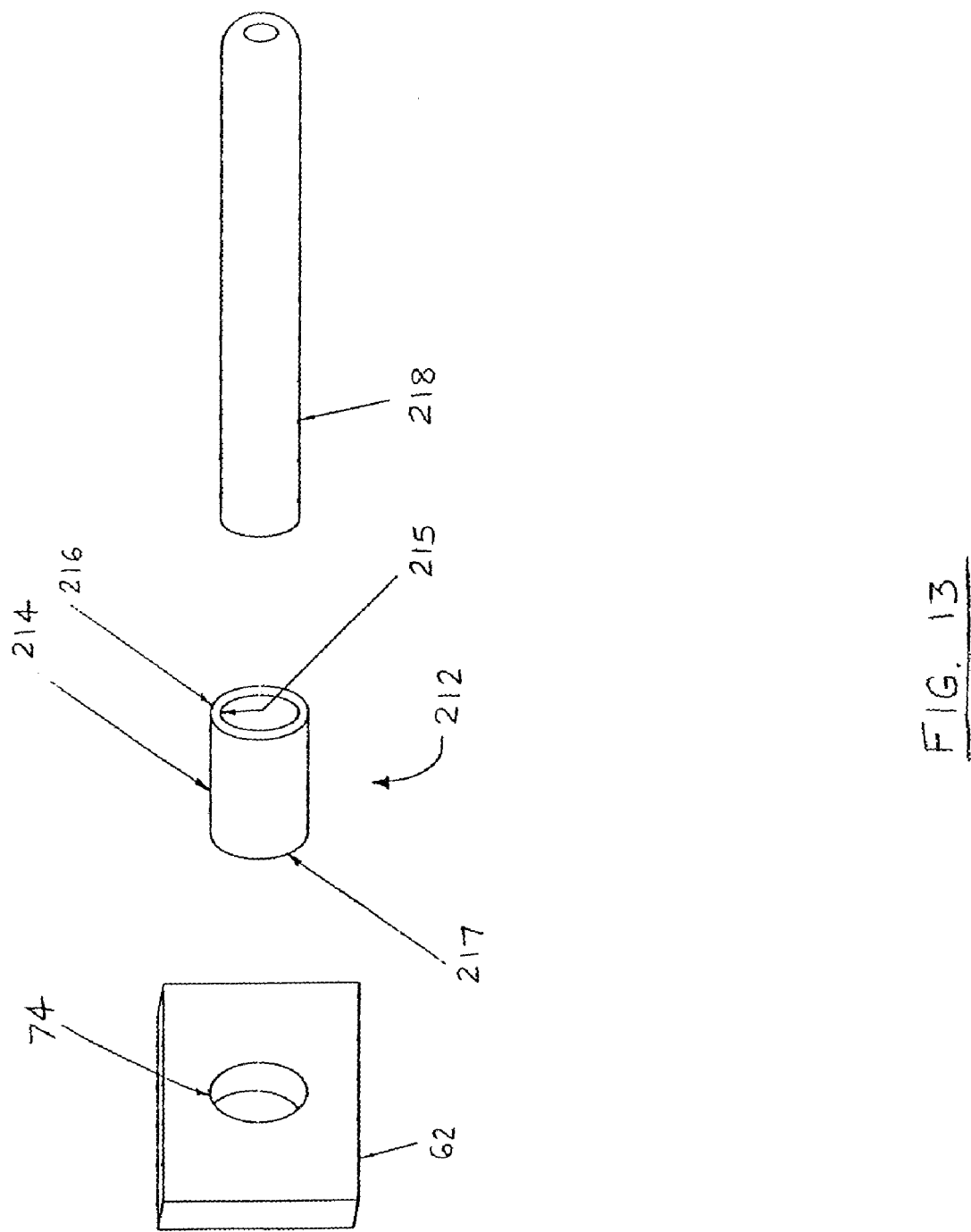
FIG. 13 is a exploded perspective view of an alternative embodiment of the present invention using a retainer to reduce manufacturing costs.

FIG. 13 depicts a partial perspective view of an alternative embodiment of a vaporizer apparatus 10 of FIG. 1 incorporating a retainer 212 for retaining a shield 218. In the alternative embodiment shown without the enclosure 12, wire assembly 14, and dimmer assembly 20, the retainer 212 is configured to be inserted into the opening 74 of the support plate or panel 62 by inserting the insertion end 216 into the opening 74. The support plate 62 function as a holding structure for holding the shield 218 within the interior space of the housing. Once disposed within the opening 74, movement of the retainer 212 is prevented by the friction between the retainer 212 and the opening 74. As is shown in FIG. 13, the shield 218, which is similar to the shield 18 of FIG. 1 except for the diameter and length dimensions, is then inserted into the retainer 212. Once the shield 218 is disposed within the retainer 212, movement of the shield 218 is prevented by the friction between the shield 218 and the retainer 212.

In the present embodiment, the shield 218 is secured differently than the shield 18 of FIG. 1. The shield 218 is secured within the opening 74 of the support plate 62 with a retainer 212 by friction rather than mounted on the heating element assembly 16 of FIG. 1. In an alternative embodiment, the shield 218 may be secured directly within the opening 74 and without the use of the retainer 212.

In one exemplary embodiment, the retainer 212 is shaped like a pipe having a generally cylindrical configuration. To facilitate insertion of the retainer 212 into the opening 74 of the support plate 62, the retainer may incorporate a tapered exterior wall 214 that tapers from the insertion end 216 tapering outwardly towards the opposite end 217. The tapered exterior surface 214 may be tapered in degrees from about 0.5 degree to 10 degrees with about 0.5 degree to about 2.7 degrees being more preferred. Alternatively, the retainer is tapered at the two ends only with the taper ranging from between about 1 degree to about 45 degrees, with about 11 degrees being more preferred Internally, the retainer interior wall 215 may similarly taper to facilitate receiving the shield 218. The interior wall 215 may taper inwardly from the receiving end 217 towards the opposite end 216 at a draft angle of about 1 degree to about 10 degrees with about 2 degrees to about 5 degrees being more preferred. The retainer 212 is preferably made of Teflon, but may be made of any number of high temperature resistant thermoplastics or other suitable material, such as a metal.

Figure 14:
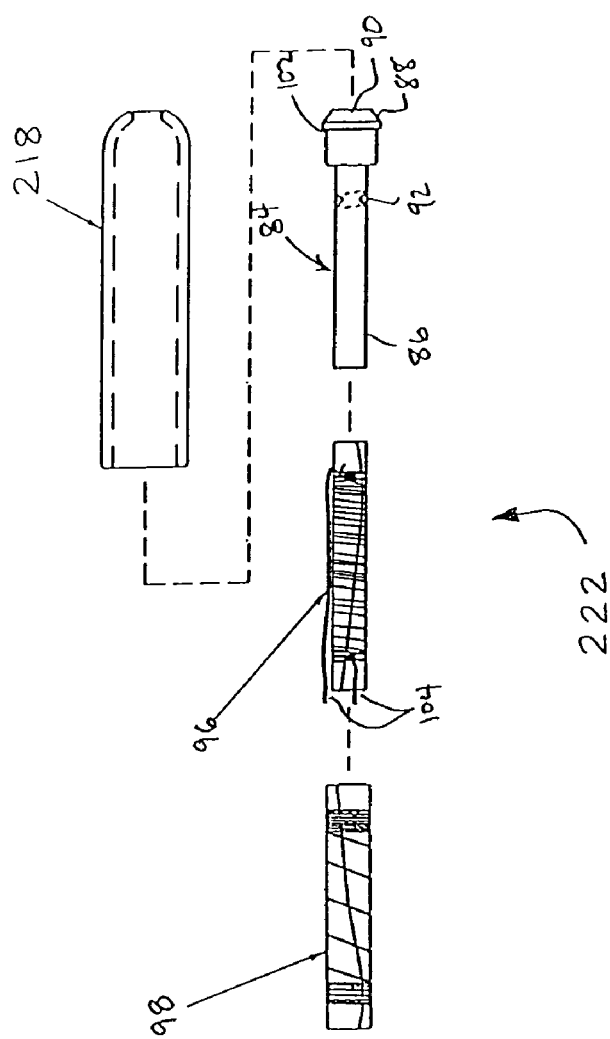
FIG. 14 is a exploded perspective view of a heating element assembly to be used in conjunction with the embodiment of FIG. 13.

FIG. 14 shows a heating element assembly 222 useable with the retainer 212 and shield 218 of the present embodiment. In one exemplary embodiment, the heating element assembly 222 includes a cylindrical shank 86, a heating coil assembly 96, and an outer insulating assembly 98. These components are the same as the components of the heating element 16 of FIG. 3.

Figure 15:
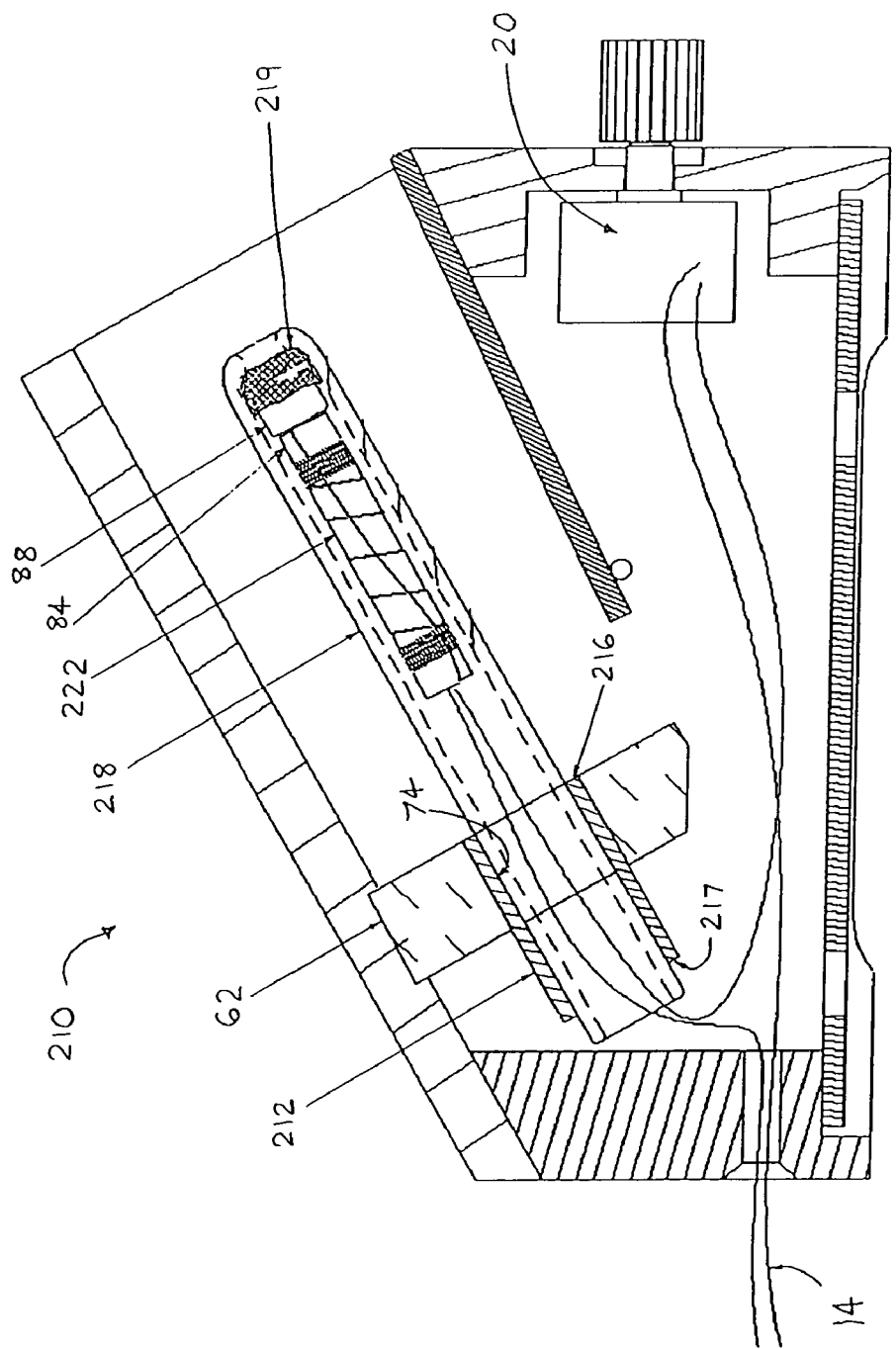
FIG. 15 is a semi-schematic perspective view of the heating element assembly of FIG. 14 and the retainer of FIG. 13.

FIG. 15 is a semi-schematic side view of the alternative vaporizer apparatus 210 comprising the retainer 212. As shown, the retainer 212 is inserted in the opening 74 of the support plate 62 via the insertion end 216. The shield 218 is inserted into the retainer 212 with the amount to be inserted being discretionary provided a sufficient length of the shield 218 is inserted into the retainer 212 to ensure adequate frictional engagement between the two. The heating element assembly 222 is inserted into the interior cavity of the shield 218 and is held within the shield 218 by frictional engagement between the cylindrical head 88 of the steel core 84 and the interior surface of the shield.

In one exemplary embodiment, a protective metal screen 220 of medium to course mesh is first wedged into the interior cavity of the shield 218 and is retained inside the shield 218 proximate the opening 219 of the shield by frictional engagement. The screen 220 may have a mesh size of about 40 mesh to about 100 mesh with 50-70 mesh being more preferred. The screen 220 is generally circular in dimension and is bent to form a cap-like structure prior to being inserted into the interior cavity of the shield 218. The cylinder head 88 of the steel core 84 of the heating element assembly 222 frictionally engages to the inside portion of the cap-like screen 220. The protective screen 220 acts as both a filter to prevent herbs from falling from the vaporizing chamber 33 of the hand piece 22 (See, e.g., FIG. 1) when the vaporizer apparatus is used and a mechanism for retaining the heating element assembly 222 within the interior cavity of the shield 218. Although not shown, coiled wires, springs, and the like may be used instead of or in addition to the screen 220 to hold the heating element. Still alternatively, a clip or other holding means for attaching to the open end of the shield 218 may be used to hold the heating element assembly within the shield.

Figure 16:
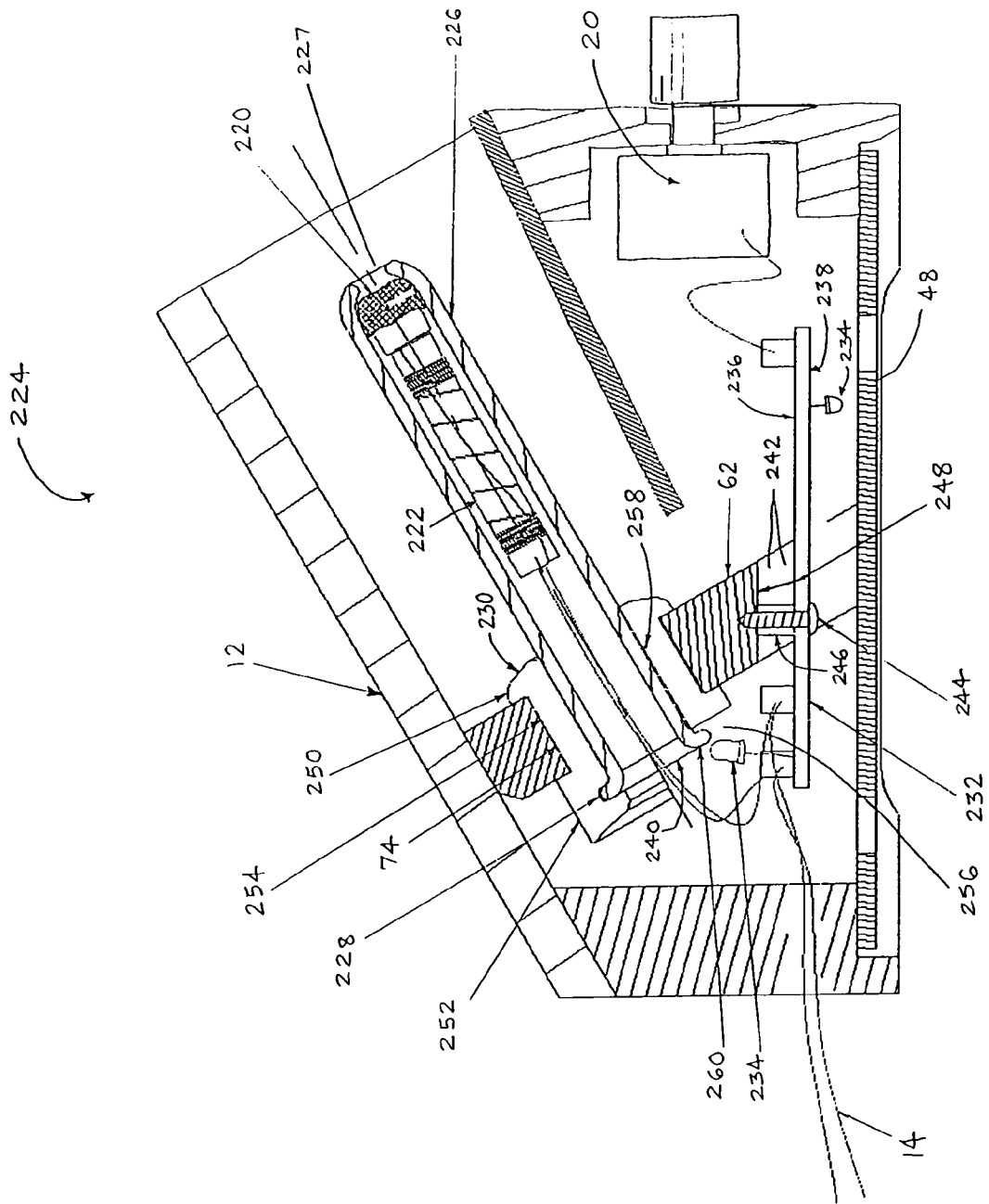
FIG. 16 is a semi-schematic cross-sectional view of the present invention showing an alternative embodiment of the retainer.

FIG. 16 shows yet another embodiment of a vaporizer apparatus 224 provided in accordance with aspects of the present invention. In the alternative vaporizer apparatus 224, a retainer 230, a circuit board 232, and one or more light emitting diodes or LEDs 234 are incorporated. The circuit board 232 allows for the electrical connection of a plurality of LEDs 234, the wire assembly 14, and the dimmer assembly 20. The one or more LEDs 234 may include a single blue, green, red color, or other colors or any combination thereof. The one or more LEDs 234 serve as an indicia of the status or intensity of the power supplied through the dimmer assembly 20 to the heating element assembly 220. As is readily apparent to a person of ordinary skill in the art, the one or more LEDs 234 may also be used for decorative purposes. In one exemplary embodiment, two LEDs 234 are incorporated. Preferably, one of the LEDs 234 is positioned on a top side 236 of the circuit board and adjacent the flared opening 240 of the shield 226 so that light emitted from the LED may irradiate through the shield and be perceived at the opening 227 of the shield by a user. Preferably, the other LED 234 is positioned on a bottom side 238 of the circuit board 232 so that the light emitted from the second LED may irradiate through the bottom panel 48 and reflect off of the surface on which the vaporizer apparatus 224 is placed for decorative purposes.

In one exemplary embodiment, a generally U-shape cut-out 242 is created in the support panel 62 for mounting the circuit board 232. One or more screws 244 and one or more spacers 246, made from wood, plastic, or metal, are then used to fasten the circuit board 232 to the support panel 62. More particularly, in one exemplary embodiment, the circuit board 232 is fastened to the horizontal portion 248 of the U-shaped cut-out 242.

In one exemplary embodiment, the retainer 230 comprises an upper flange 250 and a lower flange 252 defining an exterior channel 254. The exterior channel 254 is configured to mate with the opening 74 of the support member 62 in a detent-like engagement. The opening 74 of the support member 62 encapsulates at least a portion of the shield 226. The retainer 230 comprises a hollow opening 258 and an interior channel or retainer recess 228 on the lower flange 252.

In one exemplary embodiment, the retainer 230 is inserted into the opening 74 of the support plate 62, the shield 226 is inserted into the retainer opening 258 from the lower flange 252 and pushed forward until the curved lip 260 at the non-tapered end of the shield 226 is secured within the recess 228. The heating element assembly 222 is then positioned inside the shield 226 and secured within the shield 226 as shown and described above with reference to FIG. 14.

In an alternative embodiment, a cut-out 256 of about ⅙ to about ⅔ of the circumference of the lower flange 252 is incorporated for facilitating assembly between the flared or curved lip 260 of the shield 226 and the retainer recess 228. The cut-out 256 may be made as part of the mold for molding the retainer 230 or may be made by cutting a section of the lower flange 252 after forming the retainer. The cut-out 256 should run parallel with an edge of the retainer recess 228 and about ⅙ to about ⅔ of the circumference of the lower flange 252 in the axial or lengthwise direction to create a void or a gap for attaching the lower lip 260 of the shield 226.

The retainer 230 is made from a malleable material, preferably silicone, and is designed to fit snuggly into the opening 74 of the support plate 62. In one exemplary embodiment, silicone made commercially available from Performance Silicone, Inc. of Chino, Calif. having material part No. PSI 17-55112HT is used. However, other high temperature resistant thermoplastic elastomers or TPE compounds may be used provided they can withstand an expected operating temperature range of about 100 to about 450 degrees F. In the presently preferred embodiment, the silicone from Performance Silicone is rated for operating in between −10 degrees F. to 500 degrees F. continuous.

Figure 17:
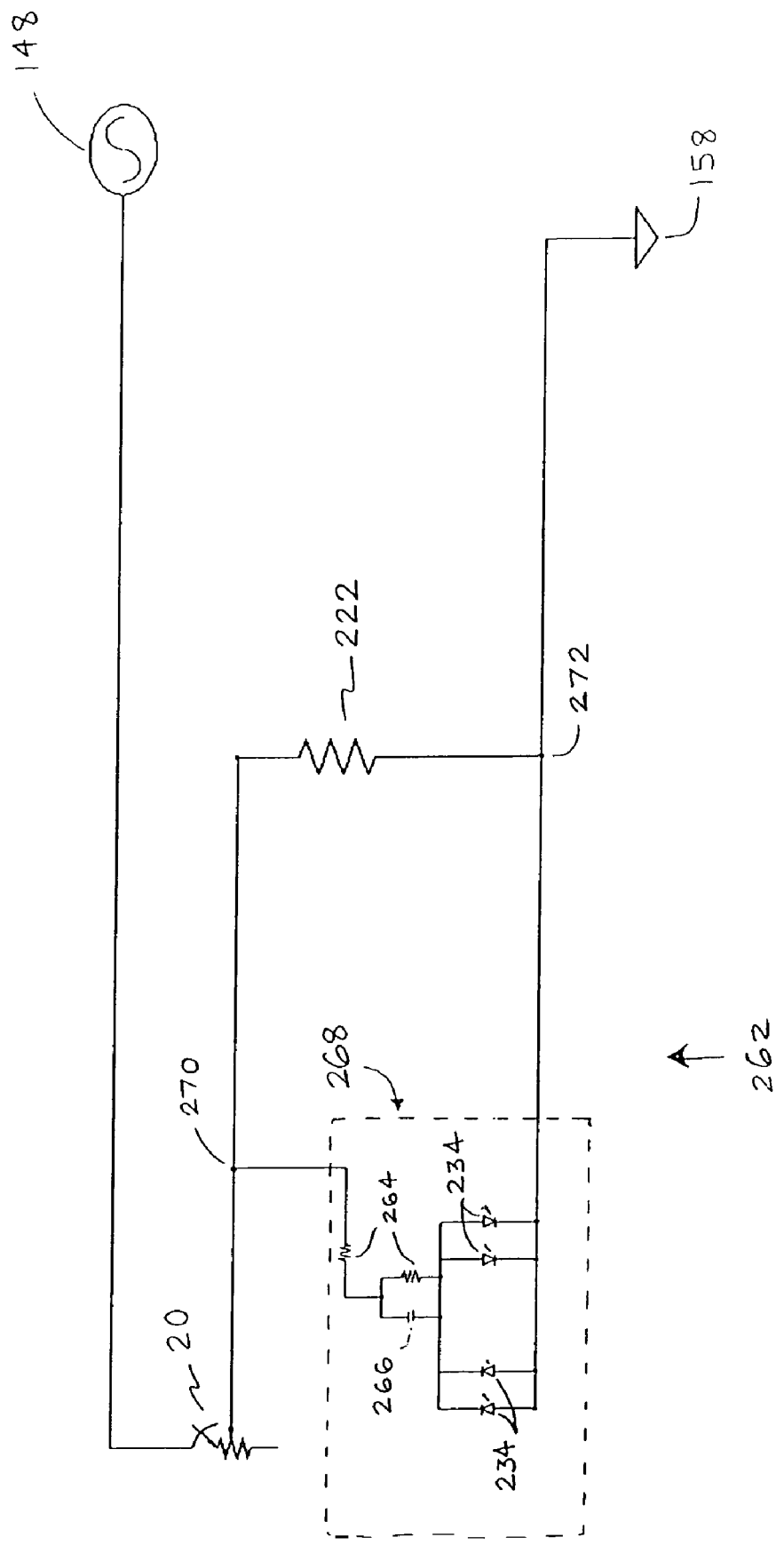
FIG. 17 is a schematic representation of an electrical circuit for the vaporizer assembly of FIG. 16.

FIG. 17 is a semi-schematic representation of the electrical wiring 262 implemented in accordance with aspects of the present invention, a portion of which is implemented on the circuit board 232 of FIG. 16. The electrical circuit 262 includes a power source 148, which is electrically connected in series to the full range dimmer switch 20. Connected to the dimmer switch 20 at node 270 are the heating element assembly 222 and an LED network 268, which is a schematic representation of the circuit implemented on circuit board 232. The LED network 268 and the heating element assembly 222 are also connected at node 272, thus providing a parallel electrical configuration. The node 272 is connected to a grounding lug 158 that grounds the entire vaporizer assembly 224. The LED network 268 may be implemented by standard printed circuit board manufacturing techniques on the circuit board 232 of FIG. 16.

The LED network 268 includes resistors 264, a capacitor 266, and one or more LEDs 234, with four shown in the wiring 262 diagram. These components are soldered to the circuit board 232. In particular, the LED network 268 connects, in series: a resistor 264, a parallel resistor-capacitor circuit consisting of another resistor 264 and capacitor 266, and a plurality of parallel LEDs 234. All other auxiliary components discussed elsewhere herein are useable with the embodiments of FIGS. 13 to 17.

Although the preferred embodiments of the invention have been described with some specificity, the description and drawings set forth herein are not intended to be delimiting, and persons of ordinary skill in the art will understand that various modifications may be made to the embodiments discussed herein without departing from the scope of the invention, and all such changes and modifications are intended to be encompassed within the appended claims. Various changes to the housing configuration, housing materials, hand piece material, etc. may be changed without substantively changing the inventive concept of the present invention. Indeed, other example of changes may include using an adapter in between the shield and the hand piece, using a different water reservoir instead of a flask, using an induced air instead of generating negative air pressure by the user, incorporating the water reservoir with the hand piece to eliminate the second flexible hose, using one housing opening instead of two or more, and using different screen retention means to filter/hold-in the herbs within the hand piece. Accordingly, many alterations and modifications may be made by those having ordinary skill in the art without deviating from the spirit and scope of the invention.

What is claimed is:

1. A vaporizer apparatus for extracting active ingredients from a specimen, the vaporizer apparatus comprising:
    a housing comprising a plurality of housing walls, an interior space defined by the plurality of housing walls, and at least one opening formed upon the housing walls, the at least one opening defining an open passage for accessing the interior space;
    a heating element assembly operable with electrical power comprising a first dimension mounted within the interior space of the housing at an angle from at least one of the plurality of housing walls;
    a shield having a body section for covering at least a portion of the heating element assembly, said shield being held in said interior space by a holding structure attached to said housing; and
    wherein said at least one opening has a second dimension larger than said first dimension for permitting an adaptor carrying the active ingredients to removably couple with the shield to communicate with the heating element.

2. The vaporizer apparatus of claim 1, wherein said holding structure comprises a support panel.

3. The holding structure of claim 2, wherein said support panel comprises an opening for receiving said shield.

4. The vaporizer apparatus of claim 1, further comprising a power regulator for regulating electrical power delivered to the heating element assembly.

5. The vaporizer apparatus of claim 1, wherein the shield has a mating section for mating with a hand piece, the mating section comprising an opening for allowing intake air to pass through.

6. The vaporizer apparatus of claim 5, wherein the hand piece comprises a vaporizing chamber for receiving a botanical specimen.

7. The vaporizer apparatus of claim 1, further comprising a retainer for holding said shield within the interior space of said housing.

8. The retainer of claim 7, wherein said retainer is made of TEFLON.

9. The retainer of claim 7, wherein said retainer is made of silicone.

10. The vaporizer apparatus of claim 1, further comprising a second housing having a water reservoir, the second housing comprises an inlet port and wherein an extension member is inserted into the inlet port.

11. The vaporizer apparatus of claim 10, further comprising a down stem, wherein the down stem is disposed within the inlet port of the second housing and the extension member is disposed within the down stem.

12. The vaporizer apparatus of claim 11, wherein the down stem comprises a stem section, a first mating section, and a second mating section; and wherein the first mating section is configured to form a seal with at least a portion of the inlet port and the second mating section is configured to form a seal with at least a portion of the extension member.

13. The vaporizer apparatus of claim 11, wherein the down stem comprises a stem. section, a first mating section, and a second mating section; and wherein the first mating section is configured to form a seal with at least a portion of the inlet port and the second mating section is configured to form a seal with an inhalation mouthpiece, which is connected to the extension member.

14. The vaporizer apparatus of claim 1, wherein the at least one opening formed upon the housing walls includes a housing opening located adjacent a power regulator.

15. The vaporizer apparatus of claim 14, wherein a mating section of the shield is oriented proximate the housing opening for mating with the adaptor.

16. The vaporizer apparatus of claim 1, further comprising a printed circuit board.

17. The vaporizer apparatus of claim 1, further comprising a light emitting diode.

18. The shield of claim 1, wherein the shield is made of glass.

19. The vaporizer apparatus of claim 1, further comprising an attachment device for vaporizing essential fluids.

20. A vaporizer apparatus for extracting essences from a medicinal carrier, the apparatus comprising:
    a heating element assembly operable with electrical power having a first maximum cross-sectional dimension;
    a shield having a substantially cylindrical body section, an exterior surface, and an interior surface defining an interior cavity having the heating element assembly disposed, at least in part, therein;
    a housing defining an interior space having at least one opening of a second maximum cross-sectional dimension;
    wherein said shield is held within said interior space of said housing by a passage of a retainer having a first open end and an opposed second open end; and wherein said second maximum cross-sectional dimension is larger than said first cross-sectional dimension for permitting an adaptor carrying the medicinal carriers to removably couple with the shield to communicate with the heating element; and wherein the heating element assembly is mounted within the interior space of the housing at an angle from vertical.

21. The vaporizer apparatus of claim 20, further comprising a power regulator for regulating electrical power delivered to the heating element assembly.

22. The vaporizer apparatus of claim 21, further comprising at least two openings formed upon the housing walls, wherein the at least two openings include a housing opening located adjacent the power regulator and a ventilation opening disposed on at least one of the housing walls.

23. The vaporizer apparatus of claim 22, wherein the mating section of the shield is oriented proximate the housing opening.

24. The vaporizer apparatus of claim 20, wherein the shield has a mating section for mating with a hand piece, the mating section comprising an opening for allowing intake air to pass through.

25. The vaporizer apparatus of claim 24, wherein the hand piece comprises a vaporizing chamber for receiving the botanical specimen.

26. The vaporizer apparatus of claim 20, further comprising a retainer for holding said shield within the interior space of said housing.

27. The retainer of claim 26, wherein said retainer is made of TEFLON.

28. The retainer of claim 26, wherein said retainer is made of silicone.

29. The vaporizer apparatus of claim 20, further comprising a second housing having a water reservoir, the second housing comprises an inlet port and wherein an extension member is inserted into the inlet port.

30. The vaporizer apparatus of claim 29, further comprising a down stem, wherein the down stem is disposed within the inlet port of the second housing and the extension member is disposed within the down stem.

31. The vaporizer apparatus of claim 30, wherein the down stem comprises a stem section, a first mating section, and a second mating section; and wherein the first mating section is configured to form a seal with at least a portion of the inlet port and the second mating section is configured to form a seal with at least a portion of the extension member.

32. The vaporizer apparatus of claim 30, wherein the down stem comprises a stem section, a first mating section, and a second mating section; and wherein the first mating section is configured to form a seal with at least a portion of the inlet port and the second mating section is configured to form a seal with an inhalation mouthpiece, which is connected to the extension member.

33. The vaporizer apparatus of claim 20, further comprising a printed circuit board.

34. The vaporizer apparatus of claim 20, further comprising a light emitting diode.

35. The shield of claim 20, wherein the shield is made of glass.

36. The vaporizer apparatus of claim 20, further comprising an attachment device for vaporizing essential fluids.

* * * * *